US012788569B2

(12) United States Patent
Kulper et al.

(10) Patent No.: US 12,788,569 B2
(45) **Date of Patent: *Nov. 10, 2026**

(54) BONE MODEL, MODELLING PROCESS AND SYSTEM THEREFOR

(71) Applicant: VERSITECH LIMITED, Hong Kong (CN)

(72) Inventors: Sloan Austin Kulper, Hong Kong (CN); Hing Wan Alfonso Ngan, Hong Kong (CN); Christian Xinshuo Fang, Hong Kong (CN); Margaret Guo, Menlo Park, CA (US); Weijia William Lu, Hong Kong (CN); Ka Li Frankie Leung, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 313 days.

This patent is subject to a terminal disclaimer.

(21) Appl. No.: 18/532,792

(22) Filed: Dec. 7, 2023

(65) Prior Publication Data

US 2024/0325155 A1 Oct. 3, 2024

Related U.S. Application Data

(63) Continuation of application No. 16/645,424, filed as application No. PCT/CN2017/100889 on Sep. 7, 2017, now Pat. No. 11,864,978.

(51) Int. Cl.
*A61F 2/30* (2006.01)
*G06F 30/20* (2020.01)
(Continued)

(52) U.S. Cl.
CPC .......... *A61F 2/30942* (2013.01); *G06F 30/20* (2020.01); *G16H 10/60* (2018.01);
(Continued)

(58) Field of Classification Search
CPC ... A61B 17/3468; A61B 17/686; A61B 17/80; A61B 2034/102; A61B 5/4851; A61B 17/809; A61B 17/7074
See application file for complete search history.

(56) References Cited

U.S. PATENT DOCUMENTS

| | | | | |
|---|---|---|---|---|
| 6,126,234 A * | 10/2000 | Cabagnero | A47D 13/02 | 297/316 |
| 7,747,895 B2 * | 6/2010 | Archer | G06F 11/2242 | 714/4.1 |

(Continued)

*Primary Examiner* — Andrew Yang
(74) *Attorney, Agent, or Firm* — JCIP; Joseph G. Chu

(57) ABSTRACT

A computer-implemented bone-implant system evaluation method for application of mesh-free analysis of a bone-implant system for evaluation of performance of a bone-implant system for an implant implanted within the bone structure at an anatomical site, said method comprising (i) receiving a set of bone structure data set, wherein set of bone structure data includes data indicative of the bone structure at an anatomical site; (ii) inputting an implant data set and inputting the position of the implant data set, wherein the implant is selected based upon the biomechanical requirements for the anatomical site and the position and of the implant data set is indicative of the position of the implant with respect to the anatomical site, wherein implant data set includes data representative of the geometry and materials properties of the implant; (iii) creating a bone-implant model, wherein said bone implant-model includes a mesh-free model of trabecular bone at the anatomical site wherein the bone-implant model is formed from the bone structure data set from step (i) and the implant data set from step (ii), and wherein the mesh-free model of trabecular bone is indicative of the trabecular bone structure of the bone structure at the anatomical site; and (iv) determining a biomechanical result based upon computer simulated loading of the bone-implant system based upon mesh-free analysis of the bone-implant model, wherein the biomechanical (Continued)

result includes data based on the displacement of the implant relative to the bone of bone-implant model.

22 Claims, 18 Drawing Sheets

(51) Int. Cl.

| | |
|---|---|
| ***G16H 10/60*** | (2018.01) |
| ***G16H 30/40*** | (2018.01) |
| ***G16H 50/70*** | (2018.01) |

(52) U.S. Cl.

CPC ............. *G16H 30/40* (2018.01); *G16H 50/70* (2018.01); *A61F 2002/30948* (2013.01); *A61F 2002/30952* (2013.01)

(56) References Cited

U.S. PATENT DOCUMENTS

| | | | | |
|---|---|---|---|---|
| 8,854,366 | B1 * | 10/2014 | Simkins, Jr. | G06T 17/20 703/2 |
| 8,855,389 | B1 * | 10/2014 | Hoffmann | G16H 50/50 382/128 |
| 2005/0060130 | A1 * | 3/2005 | Shapiro | G06F 30/23 703/2 |
| 2019/0290361 | A1 * | 9/2019 | Shalayev | A61B 34/10 |

* cited by examiner

| | Micro CT Morphometrics | | | | | Displacement | | | | | | | | | |
|---|---|---|---|---|---|---|---|---|---|---|---|---|---|---|---|
| Specimen No. | BV/TV (%) | Tb.Sp (mm) | Tb.N $(1mm^{-1})$ | Tb.Th (mm) | Force (N) | 1mm | 2mm | 3mm | 4mm | 5mm | 6mm | 7mm | 8mm | 9mm | 10mm |
| 1 – Flat tip | 17.88 | 0.54 | 0.82 | 0.22 | Experimental | 58.3 | 57.1 | 56.3 | 84.5 | 91.0 | 72.9 | 71.8 | 68.4 | 80.6 | 84.0 |
| | | | | | SPH Simulation | 37.1 | 50.8 | 107.0 | 93.3 | 80.1 | 85.3 | 79.7 | 90.9 | 100.9 | NA |
| 2 – Flat tip | 18.21 | 0.44 | 0.96 | 0.18 | Experimental | 67.9 | 57.9 | 70.5 | 67.4 | 73.6 | 75.4 | 76.4 | 78.8 | 75.4 | 71.4 |
| | | | | | SPH Simulation | 40.5 | 49.9 | 54.9 | 70.7 | 84.7 | 113.5 | 113.3 | 107.6 | 91.1 | NA |
| 3 – Flat tip | 18.85 | 0.46 | 0.71 | 0.26 | Experimental | 52.4 | 51.2 | 61.6 | 77.3 | 99.7 | 82.6 | 90.0 | 92.2 | 89.2 | 102.8 |
| | | | | | SPH Simulation | 35.9 | 49.5 | 74.7 | 92.0 | 98.3 | 147.8 | 125.8 | 97.6 | 103.5 | NA |
| 4 – Sharp tip | 26.63 | 0.4 | 1.1 | 0.24 | Experimental | 17.2 | 40.3 | 85.4 | 120.7 | 197.9 | 236.5 | 258.3 | 242.1 | 225.3 | 232.2 |
| | | | | | SPH Simulation | 11.9 | 34.7 | 116.0 | 266.1 | 295.5 | 295.0 | 283.5 | 282.6 | NA | NA |
| 5 – Sharp tip | 27.9 | 0.3 | 1.41 | 0.19 | Experimental | 33.3 | 58.3 | 108.3 | 129.1 | 211.9 | 216.0 | 195.2 | 224.9 | 247.2 | 213.2 |
| | | | | | SPH Simulation | 24.7 | 97.5 | 202.7 | 268.3 | 279.5 | 278.1 | 270.3 | NA | NA | NA |
| 6 – Sharp tip | 30.49 | 0.45 | 1.3 | 0.23 | Experimental | 38.9 | 123.2 | 191.8 | 246.2 | 265.2 | 321.3 | 296.0 | 262.3 | 237.5 | 232.3 |
| | | | | | SPH Simulation | 21.7 | 66.6 | 196.8 | 258.8 | 294.2 | 343.3 | 340.2 | NA | NA | NA |
| | | | | | | Correlation with bone density BV/TV | | | | | | | | | |
| | | | | | Correlation Coefficient (Spearman's rho) | .594* | 0.481 | .792** | .749** | .848** | .891** | .919** | .847** | .768* | .886* |
| | | | | | p value | 0.042 | 0.114 | 0.002 | 0.005 | 0.000 | 0.000 | 0.000 | 0.002 | 0.016 | 0.019 |

*. Correlation is significant at the 0.05 level (2-tailed).

**. Correlation is significant at the 0.01 level (2-tailed).

Fig. 8

Experimental vs. Simulated Results – Force/Displacement Curves of Human Trabecular Bone Specimens

Correlation between Experimental and Simulated Results

BONE MODEL, MODELLING PROCESS AND SYSTEM THEREFOR

RELATED APPLICATIONS

This is a continuation application of U.S. application Ser. No. 16/645,424 entitled "Bone Model, Modelling Process and System Therefor" filed on Mar. 6, 2020, which is a U.S. national phase of PCT International Application No. PCT/CN2017/100889 also entitled "Bone Model, Modelling Process and System Therefor" filed on Sep. 7, 2017, the contents of which are incorporated in their entireties herein.

TECHNICAL FIELD

The present invention relates to a method and system for orthopaedic surgical planning and implant design, and in particular to method and system for orthopaedic surgical planning and implant design based on anatomic data.

BACKGROUND OF THE INVENTION

The long-term integrity and stability of a bone-implant system, such as trauma fixation, corrective surgery, joint replacement or restoration and the like, is paramount for success of clinical outcomes in surgical applications.

Orthopaedic implants, including fixation implants and prosthetic implants, are implanted within bone of a subject, and a bone-implant system must be able to withstand large stresses from typical and non-typical loading, and such loading may cause bone failure, implant-bone interface failure as well as implant failure.

Biomechanical analysis of a bone-implant system can be performed during the design process of an implant by way of biomechanical analysis of bone-implant systems. Such analysis and information derived, in addition to assisting in design, can also be utilized in clinical planning. Analytical information derived from such biomechanical analyses may aid a surgeon in selecting a preferably sized implant or implant design as well as positioning and location.

In respect of aging population subjects, assessment of structural integrity of bone may be required for surgical planning and implant design, due to loss in quality of bone stock, osteoporosis and degenerative bone disease. Subjects having such compromised bone stock, in addition to increased susceptibility to trauma and fracture, may have limitations to types of implants, and increased sensitivity to exacerbated stress, giving rise to likelihood of further complications and fracture, as well as aseptic loosening.

Osteoporotic fractures are experienced by half of women and one-quarter of men over 50 years of age, requiring deployment millions of fracture fixation devices each year. The efficacy and stability of internal fixation implants for the repair of osteoporotic fractures, is largely dependent on the ability of an implant to maintain a secure and stable hold of trabecular bone during surgical reduction and during healing.

A common complication and mode of failure of a fixation implant in osteoporotic patients is "cut-out", whereby the end or tip of an implant pushes through the trabecular bone and into surrounding tissues, such as the adjacent joint cartilage or bone due to physiological loading. Corrective, or revision, surgery is generally subsequently required, and due to damage of bone at the surgical site, there may be insufficient or compromised bone stock, causing difficulties and complications during corrective or restorative surgery.

In the case of prosthetic implants, whereby such implants are in contact with and are at least party supported by trabecular bone, subsidence or instability of such an implant may occur due to implant movement within the trabecular bone as well as bone failure. Aseptic loosening is a common problem associate with such implants, often requiring revision surgery at high cost and risk to the patient.

Within the field of biomechanics, Finite Element Analysis (FEA), also known as Finite Element Method (FEM), has been used for more than four decades to study and evaluate the mechanical behavior of orthopaedic implants such as fixation implants and prosthetic implants such as joint replacement prostheses.

The size and sophistication of biomechanical FEA models has increased significantly over the past four decades, and techniques have been used for predicting the initial mechanical environment and stability of an implant through to advanced adaptive simulations including adaptation bone remodeling.

Within the field of biomechanics, FEA is used in a similar way to in vitro tests, by running a set of analyses, typically utilizing a model of a segment of bone segment or joint under simulated physiological conditions.

The power of FEA is the ability to run multiple simulations of a bone, implant or bone-implant system to assess the performance of a device under a variety of conditions.

There has been an increasing usage of FEA in the design of experiments, probabilistic analysis techniques, as well population based modelling to account for subject and surgical variability.

To date and with the evolution of FEA biomechanics, often in conjunction with physical benchmark testing and simulation, and enhancements and progression of such FEA models, advantage is taken of increased computing power with the rapid increase in computer processing technologies, the usage of biomechanical FEA techniques

OBJECT OF THE INVENTION

It is an object of the present invention to provide a bone model, and modelling process and system thereof which overcomes or ameliorates at least some of the deficiencies as associated with the prior art.

SUMMARY OF THE INVENTION

The present invention may involve several broad forms. Embodiments of the present invention may include one or any combination of the different broad forms herein described.

In a first aspect, the present invention provides a computer-implemented bone-implant system evaluation method for application of mesh-free analysis of a bone-implant system for evaluation of performance of a bone-implant system for an implant implanted within the bone structure at an anatomical site, said method comprising:

(i) receiving a set of bone structure data set, wherein set of bone structure data includes data indicative of the bone structure at an anatomical site;

(ii) inputting an implant data set and inputting the position of the implant data set, wherein the implant is selected based upon the biomechanical requirements for the anatomical site and the position of the implant data set is indicative of the position of the implant with respect to the anatomical site, wherein implant data set includes data representative of the geometry and materials properties of the implant;

(iii) creating a bone-implant model, wherein said bone implant-model includes a mesh-free model of trabecular bone at the anatomical site wherein then bone-implant model is formed from the bone structure data set from step (i) and the implant data set from step (ii), and wherein the mesh-free model of trabecular bone is indicative of the trabecular bone structure of the bone structure at the anatomical site; and (iv) determining a biomechanical result based upon computer simulated loading of the bone-implant system based upon mesh-free analysis of the bone-implant model, wherein the biomechanical result includes data based on the displacement of the implant relative to the bone of bone-implant model.

The bone structure data may be acquired from a surgical site of a subject and the bone-implant model is a subject specific bone-implant model. Alternatively, the bone structure data may be acquired from the contralateral side of the surgical site of a subject and the bone-implant model is a subject specific bone-implant model.

Alternatively, the bone structure data may be acquired from a pre-existing data set and wherein said pre-existing data is non-subject specific and wherein the bone-implant model is non-subject specific. The pre-existing data set may be selected based upon a correlation of subject data and data of the pre-existing data set.

The subject data may data selected from the group including surgical site location, geometrical properties of the bone at the surgical site, mechanical properties of the bone at the surgical site or combinations thereof. The subject data may include data selected from the group including subject age, subject gender, subject activity level or combinations thereof.

Preferably, the bone structure data is acquired by way of a bone imaging technique.

The material properties of the trabecular bone for the mesh-free model of trabecular bone may be determined from data acquired by said bone imaging technique. The material properties of the trabecular bone for the mesh-free model of trabecular bone may be acquired from a library of pre-existing data and based on statistical analysis.

The bone structure data may be acquired by a bone imaging technique selected from the group include X-ray, Computer Tomography (CT) scan, Magnetic Resonance Imaging (MRI), Bone Mineral Density (BMD) scan including by way of Dual Energy E-Ray Absorption (DEXA).

The implant data set may be selected from a plurality of implant data sets, and wherein each implant data set of said plurality of implant data sets includes data indicative of implant type and variances thereof including implant design, implant size, implant geometry and combinations thereof.

The biomechanical result provides a surgical report indicative of the appropriateness of the implant defined by the implant data set for said biomechanical requirements for the anatomical site.

Steps (ii), (iii) and (iv) may be repeated automatically until a requisite implant data set is determined and a preferable implant positioning is obtained which provides said biomechanical requirements based on redefined parameters. Upon a requisite implant data set being determined, an implant recommendation report may be provided, wherein said implant recommendation report includes one or more of implant type, implant size, implant configuration, implant positioning, and combinations thereof.

The method may provide for assistance in implant design, wherein a first implant data set is input and the position of the first implant data set is input such that the implant is positioned at a first anatomical position, and wherein the biomechanical result includes mechanical data. The biomechanical result may include mechanical includes data in relation to the bone, the implant or the bone and the implant, including at least one of stress, strain, deflection or displacement data.

Steps (ii), (iii) and (iv) may be repeated automatically until a requisite implant data set is determined and a preferable implant positioning is obtained, based upon a set of predefined criteria.

The implant may be a component of a bone fixation system. The implant may be selected from the group including hip screws, dynamic hip screws, pedicle screw, screws, plates, rods, plate/screw assemblies, wires, bars and the like.

The implant is a prosthesis or component of a prosthesis system. The implant may be a hip replacement prosthesis for hip joints which may be total or partial hip replacements, knee implants include total knee replacement implants, partial knee replacements, shoulder implant prostheses including full and partial joint replacement prostheses, spinal fusion system and the like.

The bone structure at the anatomical site may include a bone structure selected from the group including at least a portion of a femur, vertebra or humerus and tibia.

The anatomical site may be a clinical site of a subject.

The mesh free analysis method may be selected from the group including mesh-free systems including Smoothed Particle Hydrodynamics (SPH), Element-Free Galerkin (EFG), Reproducing Kernel Particle Method (RKPM) and Discrete Element Method (DEM).

In a second aspect, the present invention provides a system for computer-implemented bone-implant system evaluation for evaluation of performance of a bone-implant system for an implant implanted within the bone structure of a subject at an anatomical site using mesh-free analysis of a bone-implant system, wherein the system includes a bone structure input interface, an implant data set input interface, a processor in communication with the bone structure data input module and in communication with the implant data set input interface, and a data output module in communication with the processor, wherein the bone structure data input module receives at least one set of bone structure data, wherein set of subject data includes data indicative of the bone structure of the subject at an anatomical site;

the implant data module receives at least one implant data set and receives data indicative of the position of the implant with respect to the anatomical site, wherein the implant is based upon the biomechanical requirements for the anatomical site, and wherein implant data set includes data representative of the geometry and materials properties of the implant;

the processor receives bone structure data from the bone structure data input module and receives implant data from the implant data input interface, and wherein the processor creates a bone-implant model wherein said bone implant-model includes a mesh-free model of trabecular bone at the anatomical site, wherein the bone-implant model is formed from the at least one bone structure data set from and from the at least one implant data set, and wherein the mesh-free model of trabecular bone is indicative of the trabecular bone structure of the bone structure at the anatomical site; and wherein the processor provides output data to the output interface, wherein the output data include a biomechanical result based upon loading of the bone-implant system based upon mesh-free analysis of the bone-implant model, wherein the biomechanical result includes data based on the displacement of the implant relative to the bone of bone-implant model.

The bone structure data may be acquired from surgical site of the subject and the bone-implant model is a subject specific bone-implant model. The bone structure data may be acquired from the contralateral side of the surgical site of the subject and the bone-implant model is a subject specific bone-implant model.

Alternatively, the bone structure data may be acquired from a pre-existing data set and wherein said pre-existing data is non-subject specific bone structure data and wherein the bone-implant model is non-subject specific, and wherein the system further includes a data store in communication with the processor and carries said a pre-existing data set. The pre-existing data set may be selected by the processor based upon a correlation of subject data and data of the pre-existing data set.

The subject data may include data selected from the group including surgical site location, geometrical properties of the bone at the surgical site, mechanical properties of the bone at the surgical site or combinations thereof.

The subject data may include data selected from the group including subject age, subject gender, subject activity level or combinations thereof.

The bone structure data is data preferably acquired by way of a bone imaging technique.

The material properties of the trabecular bone for the mesh-free model of trabecular bone may be determined from data acquired by said bone imaging technique. The material properties of the trabecular bone for the mesh-free model of trabecular bone may be acquired from a library of pre-existing data and based on statistical analysis.

The bone structure data may be acquired by a bone imaging technique selected from the group include X-ray, Computer Tomography (CT) scan, Magnetic Resonance Imaging (MRI), Bone Mineral Density (BMD) scan including by way of Dual Energy E-Ray Absorption (DEXA).

The implant data set may be selected from a plurality of implant data sets, and wherein each implant data set of said plurality of implant data sets includes data indicative of implant type and variances thereof including implant design, implant size, implant geometry and combinations thereof.

The biomechanical result may be a surgical report indicative of the appropriateness of the implant defined by the implant data set for said biomechanical requirements for the anatomical site.

The processor may select an implant data set from a plurality of implant data sets and may determine the mechanical properties of the bone, implant or bone and implant based on the displacement of the implant repetitively and automatically until a requisite implant data set is determined and a preferable implant positioning is obtained which provides said biomechanical requirements based on predefined design parameters. Upon an and a requisite implant data set being determined, a biomechanical report may be provided by the processor which include an implant recommendation report, wherein said implant recommendation report includes one or more of implant type, implant size, implant configuration, implant positioning, and combinations thereof.

The system may provide for assistance in implant design, wherein a first implant data set is input and the position of the first implant data set is input such that the implant is positioned at a first anatomical position, and wherein the biomechanical result includes mechanical data. The biomechanical result may include mechanical includes data in relation to the bone, the implant or the bone and the implant, including at least one of stress, strain, deflection or displacement data.

The processor may determine the mechanical properties of the bone, implant or bone and implant based on the displacement of the implant repetitively and automatically until a requisite implant data set is determined and a preferable implant positioning is obtained which provides said biomechanical requirements based on predefined design parameters The implant may be a component of a bone fixation system, and the implant may be selected from the group including hip screws, dynamic hip screws, pedicle screw, screws, plates, rods, plate/screw assemblies, wires, bars and the like.

The implant may be a prosthesis or component of a prosthesis system, and implant may be a hip replacement prosthesis for hip joints which may be total or partial hip replacements, knee implants include total knee replacement implants, partial knee replacements, shoulder implant prostheses including full and partial joint replacement prostheses, spinal fusion system and the like.

The bone structure at the surgical site may include a bone structure selected from the group including at least a portion of a femur, vertebra or humerus and tibia.

The mesh free analysis method may be selected from the group including mesh-free systems Smoothed Particle Hydrodynamics (SPH), Element-Free Galerkin (EFG), Reproducing Kernel Particle Method (RKPM) and Discrete Element Method (DEM).

In a third aspect, the biomechanical result is provided by the method of the first aspect.

In a fourth aspect, the invention provides a computerized system for implementing evaluation of a bone-implant system, said computerized system, using mesh-free analysis of the bone-implant system for evaluation of performance of the bone-implant system for an implant implanted within the bone structure at an anatomical site, said computerized system including at least one of a processor module, an input/output module, and an interface module, and the system is configured for performing the steps of:

(i) receiving by the input/output module a set of bone structure data set, wherein set of bone structure data includes data indicative of the bone structure at an anatomical site;

(ii) receiving an implant data set and inputting the position of the implant data set input/output module, wherein the implant is selected based upon the biomechanical requirements for the anatomical site and the position and of the implant data set is indicative of the position of the implant with respect to the anatomical site, wherein implant data set includes data representative of the geometry and materials properties of the implant;

(iii) creating a bone-implant model by the processor module, wherein said bone implant-model includes a mesh-free model of trabecular bone at the anatomical site wherein the bone-implant model is formed from the bone structure data set from step 1 (*i*) and the implant data set from step (ii), and wherein the mesh-free model of trabecular bone is indicative of the trabecular bone structure of the bone structure at the anatomical site; and (iv) determining by the processor module a biomechanical result based upon computer simulated loading of the bone-implant system based upon mesh-free analysis of the bone-implant model, wherein the biomechanical result includes data based on the displacement of the implant relative to the bone of bone-implant model.

BRIEF DESCRIPTION OF THE DRAWINGS

The present invention will become more fully understood from the following detailed description of a preferred but non-limiting embodiment thereof, described in connection with the accompanying drawings, wherein:

FIG. 8 shows detailed tabulated data MicroCT morphometry data: Bone Volume (BV), Bone Volume/Total Volume (BV/TV), Trabecular Thickness (Tb.Th), Trabecular Spacing (Tb.Sp), Trabecular Number (Tb.N), Force measured per each 1 mm displacement and Correlation between BV/TV and Force for the pooled data;

FIGS. 9(*d*)-9(*f*), there is shown analysis of microCT images of human trabecular bone specimens in the experimental model using a flat-tipped indenter;

FIGS. 12(*d*) to 12(*f*), there is shown a comparison between Force versus Displacement simulation data and experimental data for the conical-tipped indenter for three human trabecular bone models;

FIG. 13(*b*) shows a Bland-Altman plot for correlation between experimental data.

DETAILED DESCRIPTION OF THE PREFERRED EMBODIMENTS

Figure 1:
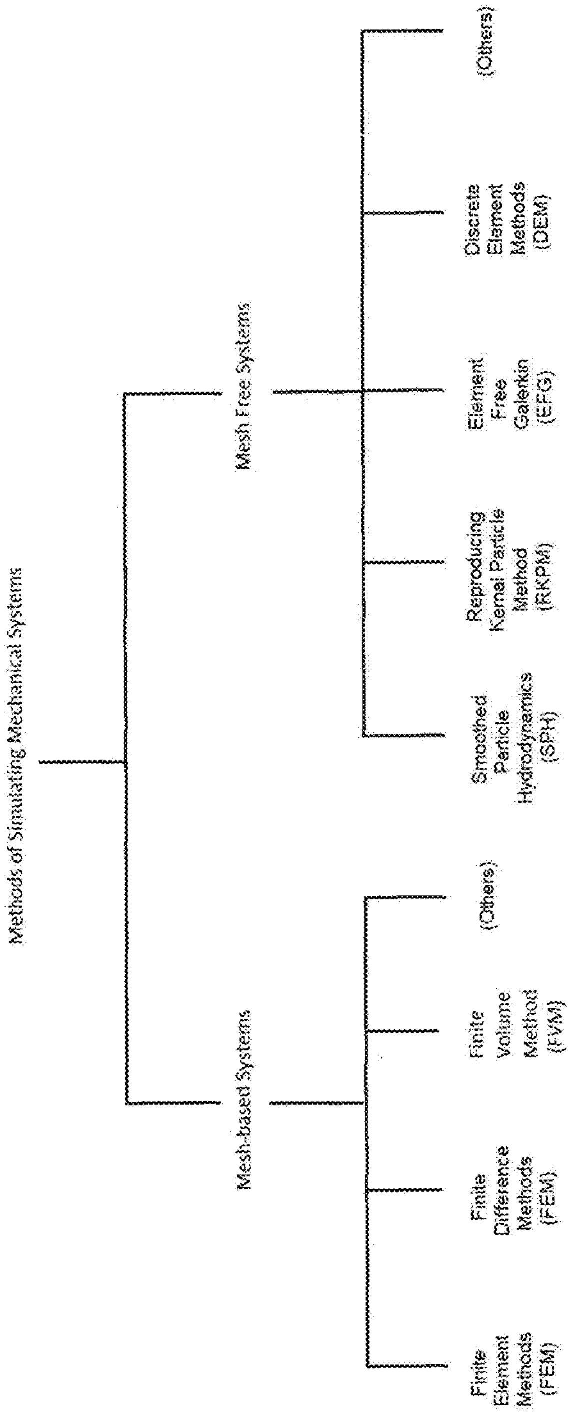
FIG. 1 shows a representation of the dichotomy of mesh-based systems as utilized in biomechanical bone-system of the prior art and mesh-free system as applicable to the present invention.

The present invention relates to a method and system for orthopaedic surgical planning and implant design, and in particular to a method and system for orthopaedic surgical planning and implant design based on anatomic data.

The present invention provides a system for modeling the mechanical behavior of bone and bone fixation implants and devices for internal fixation of bone which are inserted in trabecular bone.

The system of the present invention is also applicable for modelling the mechanical behavior of prosthetic implants, in addition to fixation implants, when affixed within bone including trabecular bone.

Both fixation implants and prosthetic implant are required to be maintained in a requisite location within the bone of a subject, and migration of such implants following surgical implantation is an undesirable effect, leading to clinical complications.

In the case of fixation implants, migration within bone can cause clinical complications such as non-union of fractures, union of bone in displaced locations, or what is termed "cut out" whereby an implant may migrate to an extent so as penetrate the outer cortex of the bone in which it is implanted.

In the case of prosthetic implants, migration of implants and aseptic loosening of implants cause clinical complications, such as increased wear of implant systems as well as potentially fracture of the implant or bone, which results in the requirement for revision surgery and associated complications.

The present system is useful in increasing the predictability of clinicians' and biomechanical engineers' predictions of the amount of migration of such an implant relative to its original position within bone tissue, as well as the likelihood of risk of "cut-out" or unwanted penetration of the implant and complications thereof when physiological or traumatic loads are applied, localized excessive loading, as well as stress shielding and/or aseptic loosening.

As such, the system can provide for:

(i) Assessment of the suitability of fixation implants for a particular clinical fixation requirement;

(ii) Selection of appropriate fixation implants for a particular clinical fixation requirement;

(iii) Assessment of suitability of prosthetic implants for a particular clinical fixation requirement;

(iv) Selection of suitable prosthetic implants for a particular clinical requirement;

(v) Design of fixation implants (vi) Design of prosthetic implants

In embodiments of the invention, the suitability of a particular implant for a subject may be assessed by direct assessment of the subject's bone stock quality by acquisition of bone properties by way of bone imaging techniques, such as X-ray, Computer Tomography (CT) scan, Magnetic Resonance Imaging (MRI), Bone Mineral Density (BMD) scan including by way of Dual Energy E-Ray Absorption (DEXA) and combinations thereof, which are then utilized by the system in order for assessment of the suitability implant for the subject.

Depending upon the surgical site and presence of trauma, such an image may be acquired from the subject's surgical site. Alternatively, such an image may be acquired from the contralateral side of the subject.

In addition to insufficient investigation as to the merits of design features of implant tips, the present inventors have also observed as well as resistance to trabecular bone penetration by other portions of an implant such as the shank of an implant, in cases lateral migration of an implant. Migration of an implant may be axial, lateral, or combinations thereof.

The basic mechanisms of implant failure and migration in trabecular bone have bene identified by the present inventors as being poorly understood within the prior art, and attempts to characterize the contribution of a design element to implant stability in trabecular bone in the prior art have been hindered by the fact that the basic mechanisms of implant failure and migration are poorly understood.

The behavior of implants migrating through porous, highly compressible cancellous bone material have few fundamental principles existing within the prior art to aid in either the design of implant or analysis of implant migration or failure of implant systems.

Within the prior art, the present inventors have found that studies have shown that basic measures of bone quality, such as mineral density and individual trabecular strength, provide relatively weak predictions of internal fixation implant failure.

Within the prior art, approaches to modeling and assessing trabecular bone have employed mesh-based methods, predominantly by way of the numerical analysis technique of finite element analysis (FEA), also known as finite element modelling (FEM). Such techniques have been used for some 40 years and are currently the predominant analytical methodology for bone, biomechanical and implant modelling, and are used for assessment of implant/bone systems for stress analysis of bone and implants, as well as implant design.

Whilst such mesh-based analytic methods are identified as useful within the art, the present inventors have identified that such analytic methods are limited in their ability to model certain key phenomena which occurs during implant migration, that is relative movement between an implant and bone.

Key phenomena identified by the present inventor which the inventors have considered to be insufficiently modelled by bone mesh-based analytical techniques of the prior art include particularly;

(i) fragmentation of bone tissue;

(ii) destructive compaction of trabecular bone tissue to the degree that the prior trabecular structure is effectively destroyed; and (iii) redistribution of fragments of fragmented bone to locations distant from their original anatomical locations.

These identified limitations by the present inventors of the utilization bone modelling methods of the prior art, whereby bone material particularly cancellous bone of a trabecular structure, include the manner in which bone tissue is represented by such a modelling method as utilized in the prior art.

When utilizing mesh-based analytical methods such as FEA/FEM techniques as used in the prior for the modelling and analysis of systems including bone tissue which comprises both cortical and cancellous bone of a trabecular form, the bone is represented as a mesh-based system as a network of interconnected nodes, each of which has a has a fixed number of predefined neighboring nodes. As such, the finite elements define elements of bone which are generally considered affixed to adjacent elements of bone of the mesh.

The theoretic background of FEA/FEM of bone models is not derived here, as those skilled in the biomechanical art are familiar with bone system FEA/FEM analytic modelling and simulation.

As observed by the present inventors, during physiological loading to an implant bone system in vivo, stress is induced in the bone, and fragmentation of bone may occur during loading as a result of implant migration within in trabecular bone or loading, which results in the production of numerous macroscopic particles formed from the constituent elements of the bone tissue, (these being bone typically of the structure of 0.1-1 mm long rods of bone called trabeculae, or small groups of trabeculae. These particles formed from fragmentation may then be redistributed to new locations as the implant continues to migrate within the bone tissue.

The present inventors have found that for bone-implant system FEA modelling, which utilizes mesh-based numerical methods, for the modelling of bone including trabecular portions, computations difficulties and errors are encountered when seeking to represent breaking and failure of trabecular bone, such as the breaking-off of nodes or groups of nodes from the original network when providing simulation of an implant/bone system.

One technique of the prior art utilized to seek to address such computations difficulties and errors has been to simply delete fragments of such bone from the system they occur. Whilst such a methodology may have some merits and usefulness in systems with small amounts of generated bone fragments from a computational standpoint and the numerical handling by such a mesh-based method, the present inventors have concluded that this can lead to substantial computational inaccuracies in cases when large quantities of bone tissue are being crushed and numerous fragments are formed and/or redistributed.

Whilst mesh-based systems have been implemented by biomechanical engineers skilled in orthopaedic biomechanics traditionally and prevalently for bone modelling including bone-implant system modelling to simulate bone for a variety of purposes, the limitations as related to trabecular bone fragmentation remain unaddressed and the shortcomings of use of such mesh systems in orthopaedic and biomechanical applications remain a limitation on analysis of such bone systems.

1. Solution Provided by the Present Invention

The present inventors have identified such shortcomings of utilization of the mesh-based bone models as used in biomechanical and orthopaedic modelling, in particular fracture of trabecular bone, and have implemented a novel bone model which overcomes the problem of fracture of trabeculae, which has not been contemplated or suggested for bone modelling within the art. In accordance with the present invention there is therefore provided a bone model including trabecular bone tissue, which utilizes computational and analytical methods that are inherently capable of representing the fragmentation and redistribution of bone material, including such fragmentation, destructive compaction, and redistribution of bone material due to and during implant migration through bone.

Accordingly and in order to address the shortcomings of the prior art and to provide a bone modelling process and system for implant selection, evaluation and an implant design system, the present invention provides a bone model which includes trabecular bone represented by a plurality of nodes or particles, in which the plurality of nodes or particles are free to interact with any neighbors they come in contact with from the system.

The present invention is distinguished from the prior art, by virtue of utilization of a bone model implementing a mesh-free model of trabecular bone and utilization of mesh-free analytical methods, whereby prior art bone models and analytic methods utilizing so-called "mesh-based" methods, particularly those based on finite element analysis (FEA).

As such, the present invention utilizes a bone model in which the trabeculae are represented as a non-meshed mode, termed "mesh-free". This is in polar contrast to bone models of the prior art which are meshed bone models which are comprised of nodes that are interconnected to a fixed number neighbors such as in FEA/FEM models, and overcomes problems and limitations as identified by the present inventors.

In the present invention, whereby trabecular bone is represented by a mesh-free model including a plurality of nodes or particles, upon simulated load for example due to the presence of an implant, these nodes or particles may be broken off, moved, and redistributed, depending on the forces and loads applied to the system.

Accordingly, the present invention provides users in the art, including clinicians and biomechanical engineers in orthopaedics, with the ability to more fully model the fragmentation, destructive compaction, and redistribution phenomena that occur during implant loading and migration.

Within the present invention, trabecular bone may be represented as nodes or particles that exist either within a domain of continuous material termed "continuous methods", or with no domain therebetween termed "discontinuous methods".

Analytical methods of modeling trabecular bone according to the present invention may include such so-called "mesh-free" methods including the analytical methods of Smoothed Particle Hydrodynamics (SPH), Element-Free Galerkin (EFG), Reproducing Kernel Particle Method (RKPM) and Discrete Element Method (DEM).

Although such "mesh-free" processes are not implemented in the art of biomechanical analysis of bone-implant systems, and the above examples of mesh-free modelling methods would not be readily known or derivable as applicable to the present subject matter by those skilled in the present art, mesh-free analytical methods are existing analytical methods used in other technical and non-related fields.

Furthermore, analytical methods referred to by the terms the Smoothed Particle Hydrodynamics (SPH), Element-Free Galerkin (EFG), Reproducing Kernel Particle Method (RKPM) and Discrete Element Method (DEM), also not readily known or derivable by those skilled in the present art, are existing mathematical modelling methods terms and processes in other technical fields.

Referring to FIG. 1, there is shown a representation of the dichotomy of mesh-based systems as utilized in biomechanical bone-system models within the present art by biomechanical engineers for analysis of bone-implant models, and mesh-free systems for analysis as utilized in the present invention.

Non-exhaustive examples of mesh-based systems include Finite Element Methods (FEM) used in biomechanical bone-system models and Finite Difference Methods (FDM).

By contrast, mesh-free systems useful with implementation of the present invention include Smoothed Particle Hydrodynamics (SPH), Element-Free Galerkin (EFG), Reproducing Kernel Particle Method (RKPM) and Discrete Element Method (DEM) as mentioned above.

In the absence of mesh-free systems within the present art, there is provided for reference in relation to Smoothed Particle Hydrodynamics (SPH), theory as discussed in "*Simulations of brittle solids using smooth particle hydrodynamics*" W. Benz, E. Asphaug, Computer Physics Communications 87 (1995) 253-265, as SPH is one of the mesh-free analytical methods applicable to the present invention and as used in exemplary embodiments of the invention as described further below.

Accordingly, the present invention provides a model and system which provides for prediction of implant performance within trabecular bone and stress analysis of greater correlation with the actual physiological system than the mesh-based bone models and systems of the prior art.

Such a model and system of present invention provides several advantages over the prior art, including:

(i) More accurate simulation of bone including trabeculae;

(ii) Increased correlation between an analytical bone model and physiological response; and (iii) Determination of dynamic response caused by loading, including fragmentation, movement and coalescence of trabeculae, and associated migration of an implant within bone.

The model and system of the present invention provides the following advantages to clinicians:

(a) Increased appropriateness of selection of a fixation implant or prosthetic implant;

(b) Ability for selection of an appropriate implant which is surgical site-specific and appropriate, for example based on analysis data from a database comprising other person's data, whereby the database comprises data acquired by way of bone imaging technique from a multitude of other subjects. The data is utilized to provide a bone model in accordance with the present invention, which includes trabeculae.

In such a case, correlation between the subject's surgical site and data from the database allows for analysis of an implant and the effect on trabeculae and migration of the implant within the bone, and selection of an appropriate implant.

In embodiments of the invention, data from the database may be a dataset selected based on a subject's personal information such as age, size and geometry of bone, and location of surgical site.

(c) Ability for selection of an appropriate implant which is surgical site specific, including in assessment, based on a subject's own trabeculae.

In such a case, data representative of the subject's bone at an adjacent the surgical site is acquired by way of a bone imaging technique, and such data is utilized by the system to form the bone model according to the invention, which includes trabeculae, and the system allows for analysis of an implant and the effect on trabeculae and migration of the implant within the bone, and selection of an appropriate implant.

Alternatively, when it is not possible or inconvenient, an image may be acquired from a contralateral surgical site of the patient, and such data used to form the bone model for analysis of an implant and the effect on trabeculae and migration of the implant within the bone, and selection of an appropriate implant.

(d) Ability to design fixation implants or prosthetic implants by consideration of the effect of fracture of trabeculae and movement of such fractures piece of bone, such the design of the fixation implants or prosthetic implants provides implants having increased compliance with their requisite biomechanical requirements.

The above provides benefit to patients, and provides for aiding in the development of safer and more clinically appropriate implants, so as to reduce the likelihood of failure of a bone-implant system resulting from implant migration, cut out, aseptic loosening, catastrophic failure or fracture of the implant from excessive loads and the like.

Those skilled in the art will understand that the term "fixation implant" may include any orthopaedic or biomechanical hardware for fixation, correct, restoration, fracture reduction of bone or the like. Such implants may include hip screws, dynamic hip screws, pedicle screw, screws, plates, rods, plate/screw assemblies, wires, bars and the like. Further, as will be understood, the term "fixation implant" is understood to include a fixation implant system, which may comprise a plurality of the forgoing implant elements.

As will also be understood by those skilled in the art, the term "prosthetic implant" includes implants which can restore the movement of joint of a subject, or provide stability of such a joint, which is fixed to bone. Such implants include hip replacement prostheses for hip joints which may be total or partial hip replacements, knee implants include total knee replacement implants and partial knee replacements, shoulder implant prostheses including full, spinal fusion systems, partial joint replacement prostheses and the like. Further, as will be understood, the term "prosthetic implant" includes implant systems and their respective elements, associated fixation elements, as well as fixation materials such as bone cement.

As is known by those skilled in the art, orthopaedic "bone cement" may be used in implant fixation for some types of prostheses such as major joint prostheses including hip, knee and shoulder prostheses, which are termed "cemented" prostheses as opposed to the "cementless" type. Such bone cement has historically and predominantly been comprised of polymethyl methacrylate or PMMA, which is prepared during a surgical procedure, by mixing pre-polymerised beads of PMMA with liquid monomer and inserted into a bone cavity in a viscous state prior to implantation of the implant, and upon curing typically within less than about 10 minutes, secures the implant. As such, the bone cement component, such as a cement mantle securing a femoral or humeral prosthesis, may be considered as part of the implant system and as such, may also be incorporated as part of an implant for assessment in accordance with the present invention as will be understood that bone cement is often in contact with trabecular bone.

Bone cement may also be used in other clinical applications, such as augmentation of bone prior to or after implantation of an implant. By way of example, bone cement has been used for augmentation of bone within the femoral head of a patient who may have a femoral neck fracture which requires reduction and/or fixation by way of a hip screw, such as a dynamic hip screw (DHS).

In such cases, bone cement may be injected into the femoral head of the patient, for example through a passage prepared for insertion of the hip screw, and prior to curing the hip screw is urged into the femoral head and secured by way of the associated place and screw assembly.

Alternatively, bone cement may be injected into the femoral head of a patient through a cannulated, fenestrated hip screw or nail for augmentation of the bone.

When introducing bone cement for bone augmentation, for example within the femoral head, the bone cement has been found to interdigitate with the trabecular bone, and provide an augmentation to somewhat reduce implant migration and somewhat reduce the likelihood of screw cut-out.

In such cases, the bone cement may also be considered part of the implant. As such, the bone cement component, may be considered as part of the implant system and as such, may also be incorporated as part of an implant for assessment in accordance with the present invention as will be understood that bone cement is often in contact with trabecular bone.

The present invention may also be useful for modelling of features of implants, such as polymeric, rubberized or elastic material portions, which also may be in contact with trabecular bone.

As such, when referring to "implants" of the present invention, this term must be understood to also include implant systems and components thereof which may be in contract with trabecular bone, such as bone cement for fixation or bone augmentation purposes, or polymeric, rubberized or elastic elements of an implant or implant system.

As will be understood, the present invention is also applicable to other types of bone cements such as bioactive bone cements, composite bone cements, glass ionomer cements and the like. Further, other deformable materials which may elements of an implant or implant system, which may be in contact with trabecular bone, are also applicable to the present invention.

According with the present invention, the above fixation implants and prosthetic implants, when deployed within a surgical environment, often will be in contact with the trabeculae of bone of a subject and as such, the present invention which utilizes a bone model including trabeculae of bone represented as a plurality of mesh-free nodes and associated mesh-free analytical process, is applicable of the assessment and prediction of the mechanical response of the bone system upon physiological loading of such implants when deployed at a surgical site within a subject.

2. Method and System of Present Invention

Figure 2A:
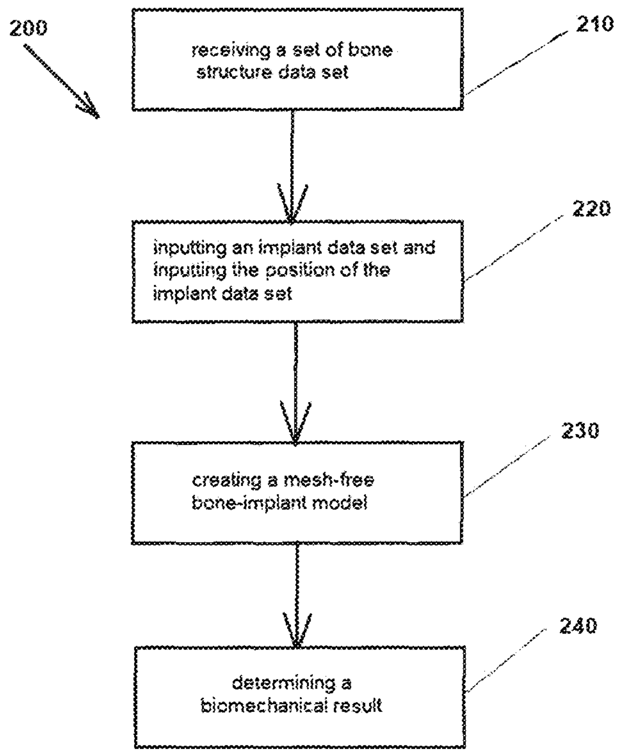
FIG. 2*a* shows a flow diagram of the method of the present invention.

Referring to FIG. 2*a*, there is shown a flow diagram of the method 200 of the present invention. The method 200 provides a computer-implemented bone-implant system evaluation method for the evaluation of the performance of a bone-implant system for an implant implanted within the bone structure at an anatomical site.

The method 200 utilizes a mesh-free analysis of a bone-implant system in accordance with the invention, for reasons including those as recited above. In particular, the novel use of a mesh-free model of trabecular bone provides the advantages of the present invention, including:

(a) Prediction of likelihood of implant migration, (b) Selectability of implant so as to minimize implant migration, and (c) Assistance in design of implants, including in relation to implant migration.

Such implants may be fixation implants, for example hip screws, dynamic hip screws, pedicle screw, screws, plates, rods, plate/screw assemblies, wires, bars and the like. Such implants may also include a prosthesis or component of a prosthesis system for example hip replacement prostheses for hip joints which may be total or partial hip replacements, knee implants include total knee replacement implants, partial knee replacements, shoulder implant prostheses including full and partial joint replacement prostheses, spinal fusion system and the like.

The method 200 includes the steps of:

(i) Receiving a Set of Bone Structure Data Set 210.

A set of bone structure data includes data indicative of the bone structure at an anatomical site.

In an embodiment of the invention for a surgical application, the process may be subject specific, and the bone-implant model based on anatomy of the subject. Alternatively, the bone structure data is acquired from the contralateral side of the surgical site of a subject.

In other embodiment as a surgical application, process may be used for either assistance in implant design or surgical planning. In such embodiments, the bone structure data may acquired from a pre-existing data set and wherein said pre-existing data is non-subject specific and wherein the bone-implant model is non-subject specific.

The pre-existing data set may be selected based upon a correlation of subject data and data of the pre-existing data set, and includes data selected from the group including surgical site location, geometrical properties of the bone at the surgical site, mechanical properties of the bone at the surgical site or combinations thereof. The data may further include subject data includes data is selected from the group including subject age, subject gender, subject activity level or combinations thereof.

In relation to the above embodiments, the bone structure data may be acquired by way of a bone imaging technique. For example, the bone structure data is acquired by a bone imaging technique selected from the group include X-ray, Computer Tomography (CT) scan, Magnetic Resonance Imaging (MRI), Bone Mineral Density (BMD) scan including by way of Dual Energy E-Ray Absorption (DEXA).

Bone data may also be automatically selected using a machine-learning algorithm that finds the most relevant match between a subject's bone data (using images and/or other parameters such as DEXA score) and an entry in this pre-existing data set.

Bone data may also be automatically generated using an algorithm that creates a typical bone structure by analyzing the subject's bone data (also using images and/or other parameters such as DEXA score).

(ii) Inputting an Implant Data Set and Inputting the Position of the Implant Data Set 220.

The implant to be used in the model of the process is selected based upon the biomechanical requirements for the anatomical site to which it is to be deployed, and the position the implant is to be deployed.

The implant data set is indicative of the position of the implant with respect to the anatomical site, wherein implant data set includes data representative of the geometry and materials properties of the implant.

In an embodiment of the invention for surgical planning, the implant data set may be selected from a plurality of implant data sets. Each implant data set of said plurality of implant data sets includes data indicative of implant type and variances thereof including implant design, implant size, implant geometry and combinations thereof.

In embodiments of the invention for the assistance in implant design for example when required mechanical data is required for implant design purposes, a user may for example enter a first implant data set is input and the position of the first implant data set is input such that the implant is positioned at a first anatomical position.

(iii) Creating a Bone-Implant Model and Inputting Loading Conditions 230.

A bone implant-model is created includes a mesh-free model of trabecular bone at the anatomical site and the implant data set, and wherein the mesh-free model of trabecular bone is indicative of the trabecular bone structure of the bone structure at the anatomical site.

The bone-implant model is formed from the bone structure data set from step 1 (*i*) and the implant data set from step (ii).

The material properties of the trabecular bone for the mesh-free model of trabecular bone may be determined from data acquired by said bone imaging technique. Alternatively, other sources of material properties may be utilized.

The material properties of the trabecular bone for the mesh-free model of trabecular bone may alternatively acquired from a library of pre-existing data and based on statistical analysis.

The mesh free analysis model and process may be selected from the group including mesh-free models include Smoothed Particle Hydrodynamics (SPH), Element-Free Galerkin (EFG), Reproducing Kernel Particle Method (RKPM) and Discrete Element Method (DEM).

Loading conditions for applications to the bone-implant model may be input, based on any of the following, alone or in combination: physiological loading data recorded from an individual subject or patient, physiological loading data recorded from a population or subjects or patients, loading data pertaining to certain movements (such as walking, running, or moving a limb or other body part in a relevant pattern), or loading data pertaining to certain types of injuries (traumatic injuries, stress injuries, and otherwise).

As is known by those skilled in the art, numerous types of loading conditions are relevant to orthopaedic research and clinical practice, including the application of both cyclical and static forces to bone-implant models.

(iv) Determining a Biomechanical Result 240.

The biomechanical result as provided by the present invention is based upon computer simulated loading of the bone-implant system based upon mesh-free analysis of the bone-implant model.

The biomechanical result includes data based on the displacement of the implant relative to the bone of bone-implant model.

In embodiments of surgical planning, the biomechanical result provides a surgical report indicative of the appropriateness of the implant defined by the implant data set for said biomechanical requirements for the anatomical site.

In such an embodiment, steps (ii), (iii) and (iv) may be repeated automatically until a requisite implant data set is determined and a preferable implant positioning is obtained which provides said biomechanical requirements based on redefined parameters.

Upon a requisite implant data set being determined, an implant recommendation report may be provided, wherein said implant recommendation report includes one or more of implant type, implant size, implant configuration, implant positioning, and combinations thereof.

In embodiments whereby the method is utilized for assistance in implant design, the biomechanical result may include mechanical data in relation to the bone, the implant or the bone and the implant, including at least one of stress, strain, deflection or displacement data.

Steps (ii), (iii) and (iv) may be repeated automatically until a requisite implant data set is determined and a preferable implant positioning is obtained, based upon a set of predefined criteria.

Figure 2B:
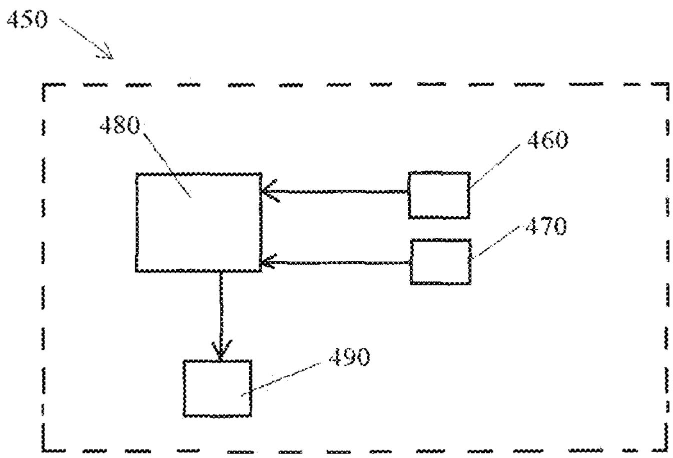
FIG. 2*b* shows a schematic representation of the system of the present invention for implementation of the method of the present invention of FIG. 2*a;*

Referring to FIG. 2*b*, there is shown a schematic representation of an embodiment of a system 450 of the present invention for implementation of the method 200 of the present invention of FIG. 2*a*.

The system 450 is computer-implemented bone-implant system modelling system, for evaluation of performance of a bone-implant system for an implant implanted within the bone structure of a subject at an anatomical site using mesh-free analysis of a bone-implant system.

In order to implement the method 200 of the invention as described with reference to FIG. 2*a*, the present system 450 includes:

(i) a bone structure input module 460, (ii) an implant data set input module 470, (iii) a processor 480 in communication with the bone structure data input module 460 and in communication with the implant data set input module 470, and (iv) a data output module 490 in communication with the processor 480.

As the method 200 of the present invention is implemented within the system 450 of the present invention:

- the bone structure data input module 460 receives at least one set of bone structure data, wherein set of subject data includes data indicative of the bone structure of the subject at an anatomical site;
- the implant data module 470 receives at least one implant data set and receives data indicative of the position of the implant with respect to the anatomical site, wherein the implant is based upon the biomechanical requirements for the anatomical site, and wherein implant data set includes data representative of the geometry and materials properties of the implant;
- the processor 480 receives bone structure data from the bone structure data input module 460 and receives implant data from the implant data input module 470;
- the processor 480 creates a bone-implant model wherein said bone implant-model includes a mesh-free model of trabecular bone at the anatomical site, wherein the bone-implant model is formed from the at least one bone structure data set from and from the at least one implant data set, and wherein the mesh-free model of trabecular bone is indicative of the trabecular bone structure of the bone structure at the anatomical site; and
- the processor provides 480 output data to the output module 490, wherein the output data include a biomechanical result based upon physiological loading of the bone-implant system based upon mesh-free analysis of the bone-implant model. The biomechanical result may include mechanical data, a surgical report, or representation of data as applicable to clinical and/or design applications.

Any one of the features of the embodiments described herein referred to as a "module" may be implemented in software for execution by various types of processors.

An identified module of executable code may, for instance, comprise one or more physical or logical blocks of computer instructions which may, for instance, be organized as an object, procedure, function, or algorithm.

The identified blocks of computer instructions need not be physically located together, but may comprise disparate instructions stored in different locations which, when joined logically together, comprise the module and achieve the stated purpose for the module.

A module may also be implemented as a hardware circuit comprising custom circuits or gate arrays, off-the-shelf semiconductors such as logic chips, transistors, or other discrete components.

A module may also be implemented in programmable hardware devices such as field programmable gate arrays, programmable array logic, programmable logic devices or the like. A module of executable code may comprise a single instruction, multiple instructions, and may be distributed over several different code segments, among different programs, and across several discrete memory devices.

Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Within an embodiment, the system 450 may be implemented on a computer system, which includes a processor for providing the method steps of the present invention.

- The bone structure data may be inputted into the computer system by way of an input module 460 which could be an electronic input via a computer network, or by way of a computer file which could be on a transferable disk device. Such data could be received raw, semi-processed, or fully processed by the system, or at least partly processes externally.
- The implant data module 470 of the system 450 may receive the implant data set electronically from a local or external data store, for example by way of a computer network. The data indicative of the position of the implant with respect to the anatomical site may be received from a user interface, such as a keyboard and mouse, or touchpad device.
- The output data is accessible via the output module 490. The data may be provided in electronic form so that it may be utilized. For example, the output data may be utilized:
- to provide a surgical report indicative of the appropriateness of the implant defined by the implant data set for the biomechanical requirements for the anatomical site, or for assistance in implant design, the biomechanical result may include mechanical data in relation to the bone, the implant or the bone and the implant, including at least one of stress, strain, deflection or displacement data.

Referring to FIG. 3*a* to FIG. 3*e*, there is shown an illustrative example of a system 500 according to the present invention, when utilized as a surgical planning implementation.

Figure 3A:
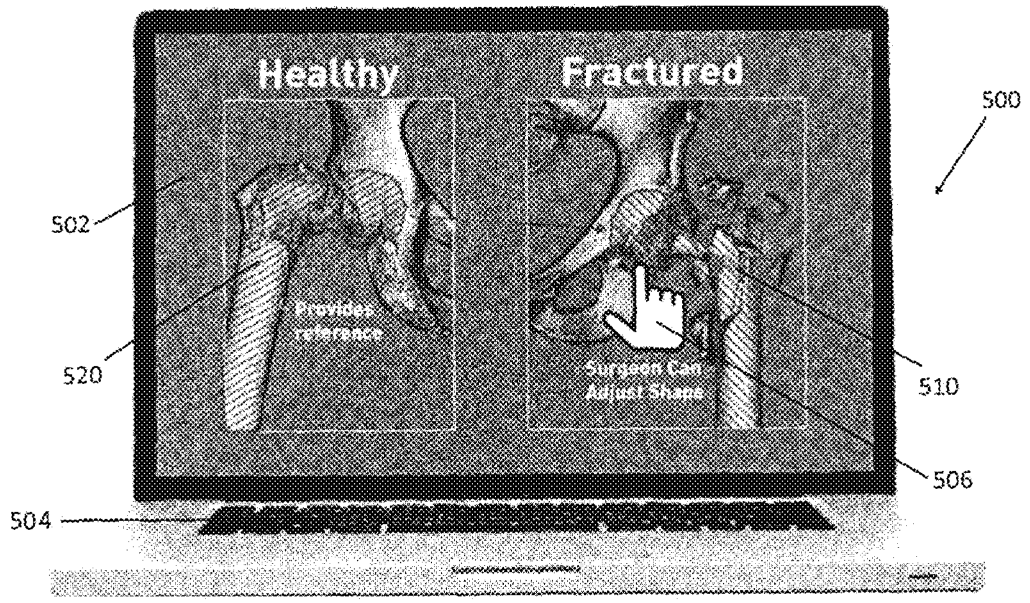
FIG. 3*a* to FIG. 3*e* show an illustrative example of a system according to the present invention, when utilized as a surgical planning implementation.

As shown in FIG. 3*a*, there is shown an image of a fractured femur 510 of a patient on a visual display unit 502, which has been acquired as a radiographic image, for example by way of a CT scanner. In the present example, a CT scan of the contralateral and healthy femur 520 is used in order to create the bone-implant model for surgical assistance. Based on the image, the surgeon can formulate a bone reduction strategy using a user interface comprised of a keyboard 504 and a selector indicator 506 on the visual display unit 502.

Figure 3B:
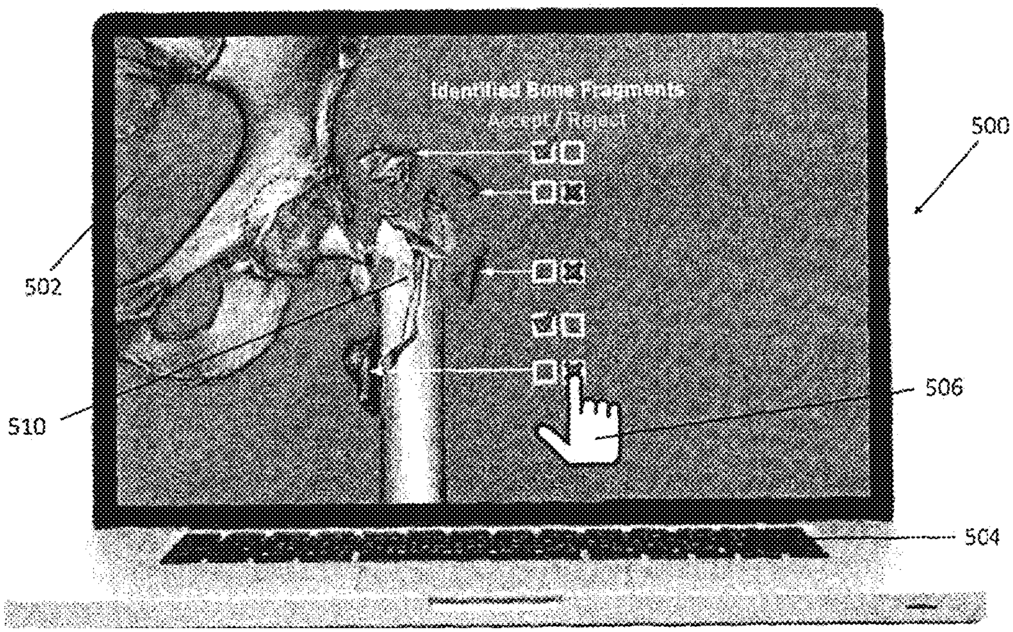

Referring to FIG. 3*b*, in the present example the system 500 may provide the option for a surgeon to exclude and select bone fragments for the reduction of the fracture for example by way of the selector indicator 506. As this step is optional, it may not necessarily be available in other or alternate embodiments of the invention.

Figure 3C:
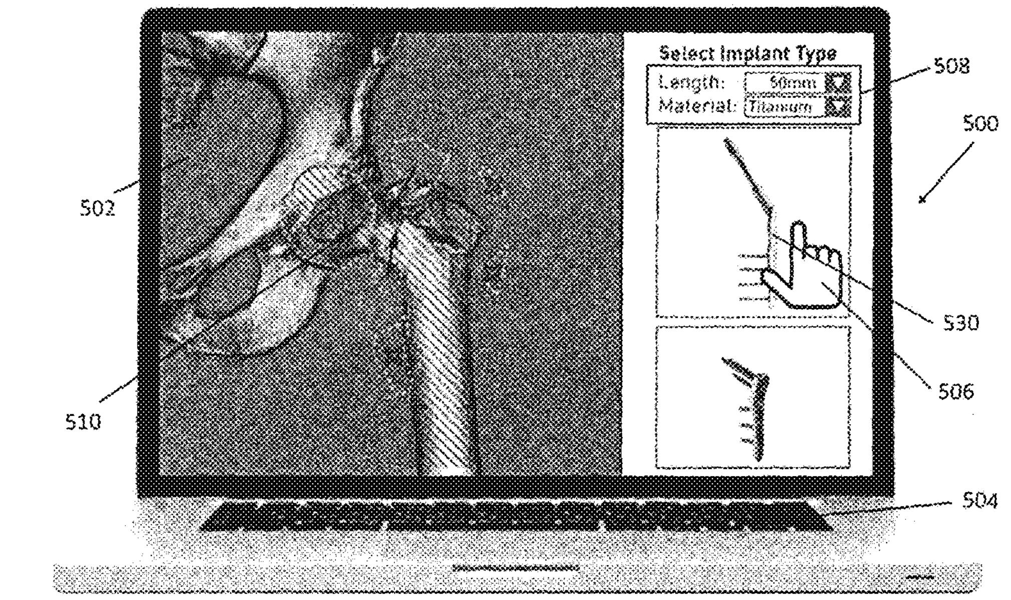

Referring to FIG. 3*c*, optionally an in the present embodiment, the system 500 may automatically align bone fragments so as to provide a model of a reduced fracture of the femur 510. Alternatively, the surgeon may reduce the fracture on the visual display unit 502 manually using the selector indicator 506.

Figure 3D:
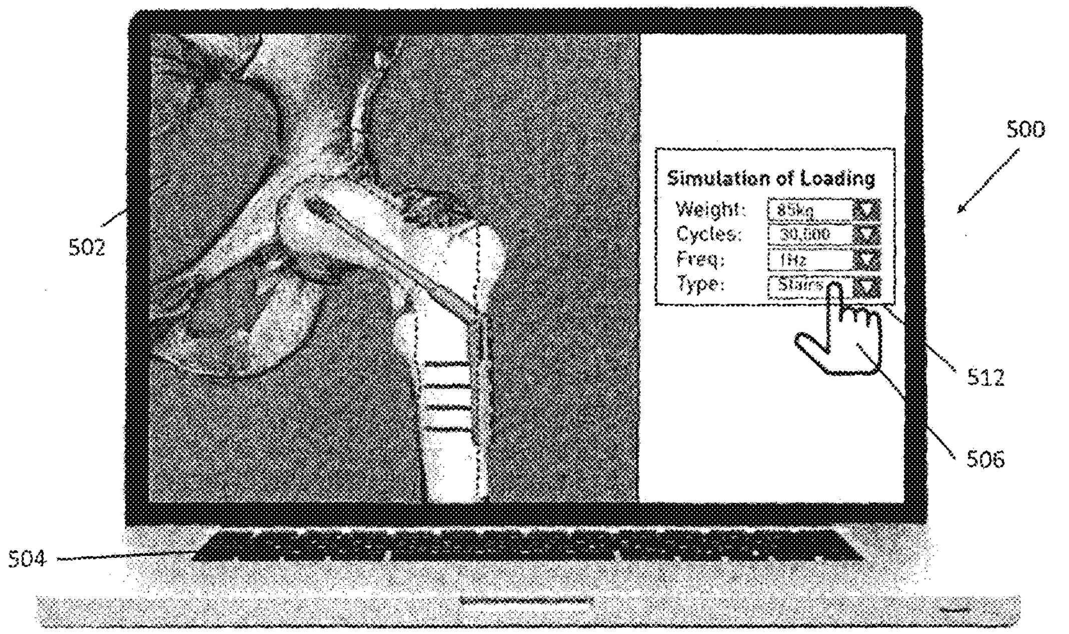

The surgeon then selects a requisite implant 530 by the selector indicator 506 from a library of implants held in a datastore which is part of the system 500 or in communication with the system 500 and the size thereof an optionally the material 508, for example Referring to FIG. 3*d*, the implant 530 is located by the surgeon or automatically with the surgical site of the fractured femur 510. The surgeon may then select loading and physiological parameters, such as patient weight, number of cycles, frequency and activity regime 512 via selector indicator 506. Alternatively, the system 500 may automatically provide the loading and physiological parameters, as a standard or from an applicable electronic library.

From the input datasets, a mesh-free analytical model is created using the CT data from the contralateral femur to provide a model including a mesh-free trabecular bone model, and the implant data based on the surgeon's selection as described in FIG. 3*c*. The loading is applied based on the loading and physiological parameters as selected.

Figure 3E:
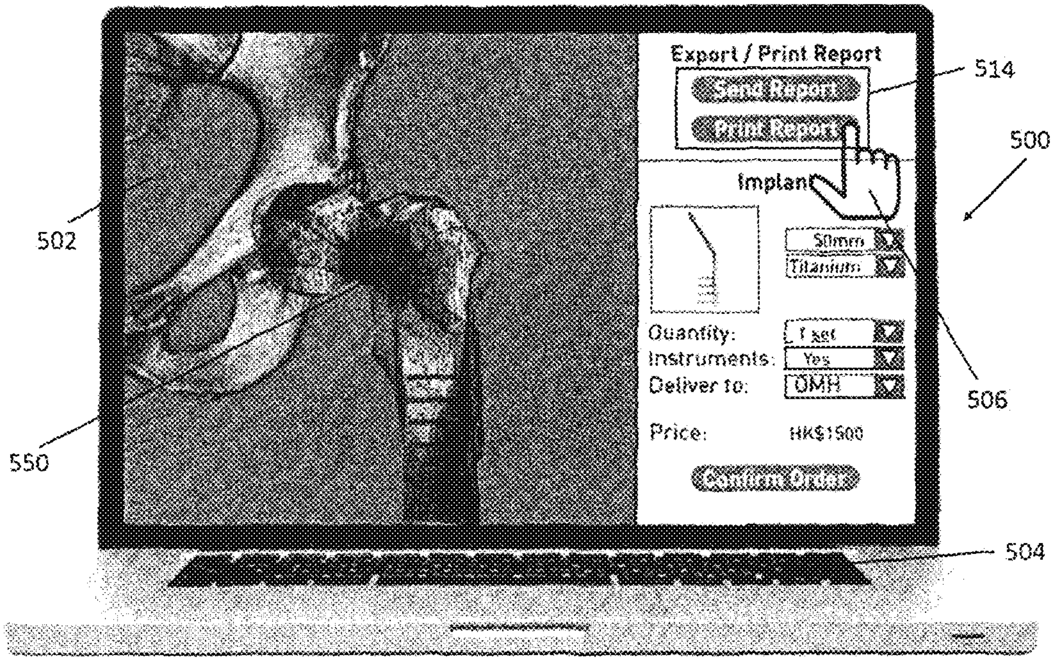

Referring to FIG. 3*e*, the surgeon may then select to have a surgical report provided by selection at 514 by the selector indicator 506. Further, results from analysis as provided by the mesh-free model can be represented graphically 560 on the visual display unit 502, whereby mechanical outcomes may be displayed, such stress, strain, displacement.

The surgical report may provide a surgeon with the outcome of the model for the surgical example as shown. The surgical report may provide recommendations such as whether the bone-implant system 500 is susceptible to failure, amount or likelihood of implant migration or the like.

In some embodiments, the step of implant selection may be automatic, and repeated until a requisite result within predefined parameters is reached.

In other embodiments, the system may be used for implant design and assessment, in contrast to the exemplary surgical planning example.

3. Assessment of Applicability of Mesh-Free Bone-Implant Model

In order to assess the applicability of mesh-free modelling of trabecular bone, the simulation results when predicting the behavior of an implant when penetrating and crushing bone tissue compared to empirical results, using human bone and synthetic bone, as well as the results generated by conventional computer based methods (FEA) for predicting the behavior of implants used to fix osteoporotic fractures, a mesh-free model for simulation of the bone-implant system provided excellent predictive results, in particularly with respect to the prediction of the location and magnitude of bone compaction and densification.

In contrast, conventional computational models of bone did not match the synthetic nor cadaveric bone while testing the bone compaction.

In the study, using a discrete element method (DEM) of particles governed by Hertzian and JKR contact theories, a 10.5×10.5×21 mm bone-like substrate was modelled as a porous 3D particle network. A simulated 100N load was applied to the substrate via 5 mm diameter implants with various implant tip designs.

These simulations were then repeated under identical conditions using the commercial FEA software ABAQUS.

Empirical validation experiments using human cadaveric bone from the proximal human femur (female>75 years) and artificial bone (polyurethane foam 0.16 g/cc) were conducted under microCT and high resolution video. NCORR, an open source 2D digital image correlation MATLAB program was used to extract fracture patterns and changes in density from the image data, with significant differences found ($p<0.01$) between implant tip designs.

Figure 4A:
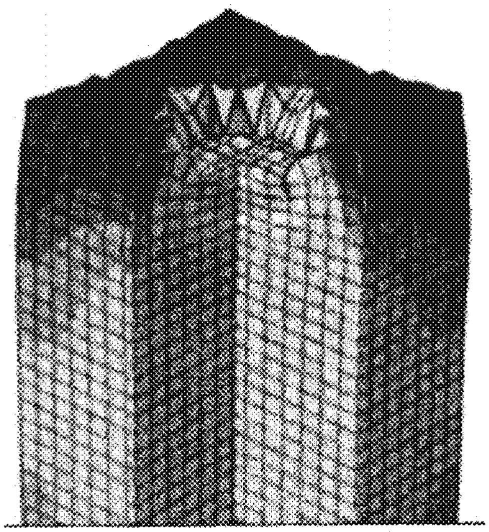
FIGS. 4*a* and 4*b* show and experimental comparison between a mesh-based modelling method of FEA of the prior art in FIG. 4*a* in and the experimental model using polyurethane foam as artificial bone in FIG. 4*b* using an indenter with a flat tip.
Figure 4B:
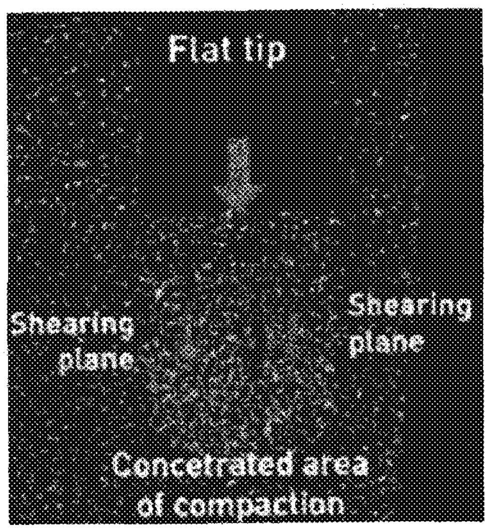

As shown in FIGS. 4*a* and 4*b*, whereby experiments were conducted using an indenter with a flat tip using the mesh-based modelling method of FEA of the prior art in FIG. 4*a* in and the experimental model using polyurethane foam as artificial bone, whilst there was deformation in the FEA model, there is no compaction or account for fracture, and the density remains unchanged, unlike in the experimental model of FIG. 4*b*.

Figure 4C:
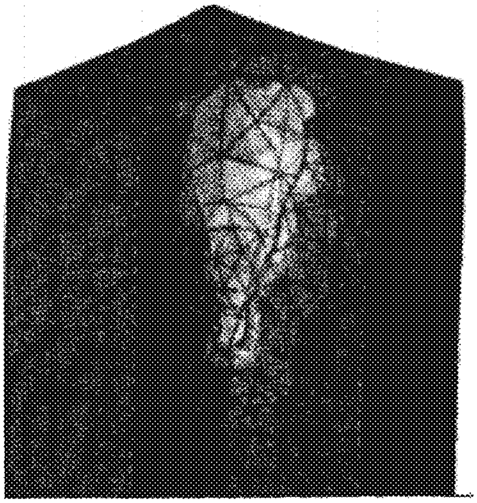
FIGS. 4*c* and 4*d* show and experimental comparison between a mesh-based modelling method of FEA of the prior art in FIG. 4*c* in and the experimental model using polyurethane foam as artificial bone in FIG. 4*d* using an indenter with a conical tip.
Figure 4D:
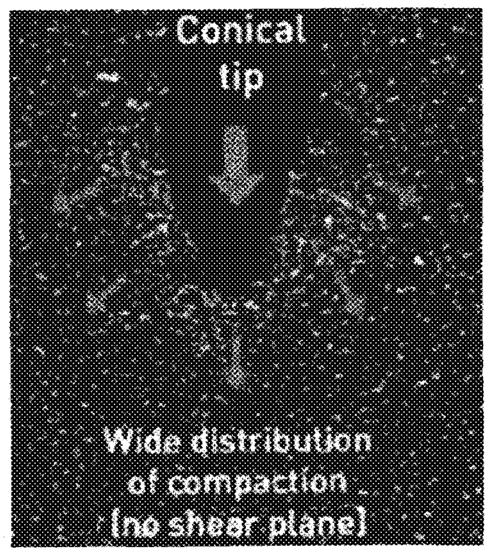

Similarly as shown in FIGS. 4*c* and 4*d*, whereby experiments were conducted using an indenter with a conical tip using the mesh-based modelling method of FEA of the prior art in FIG. 4*c* in and the experimental model using polyurethane foam as artificial bone, whilst there was deformation in the FEA model, there is no compaction or account for fracture, and the density remains unchanged, unlike in the experimental model of FIG. 4*d*.

As was shown, the experimental model using and a conical tip, conventional (FEA) simulations failed to predict these differences in density, whilst grossly overestimating strain on the bulk substrate and underestimating local shearing and compaction adjacent to the implant.

Figure 5B:
FIGS. 5*a* and 5*b* show a comparison of a DEM simulated model FIG. 5*a* with experimental results for a flat-tipped indenter of diameter 5 mm advanced into artificial bone comprised of polyurethane foam in FIG. 5*b*.
Figure 5A:
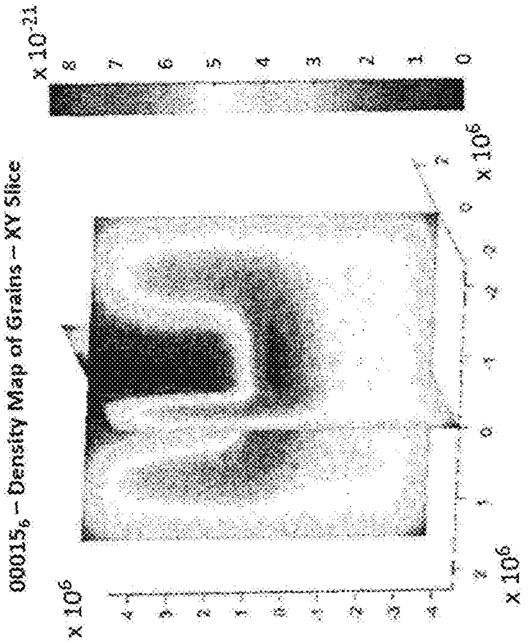

As shown in FIGS. 5*a* and 5*b*, the DEM simulated model results are shown in FIG. 5*a* in comparison with experimental results for a flat-tipped indenter of diameter 5 mm advanced into artificial bone comprised of polyurethane foam in FIG. 5*b*.

Figure 6B:
FIGS. 6*a* and 6*b* show a comparison of a DEM simulated model FIG. 6*a* with experimental results for a conical-tipped indenter of diameter 5 mm advanced into artificial bone comprised of polyurethane foam in FIG. 6*b*.
Figure 6A:
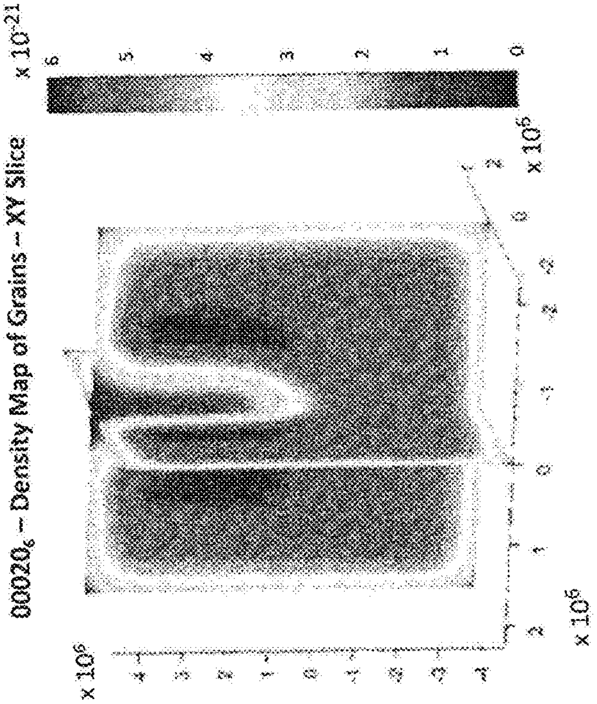

As shown in FIGS. 6*a* and 6*b*, the DEM simulated model results are shown in FIG. 6*a* in comparison with experimental results for a flat-tipped indenter of diameter 5 mm advanced into artificial bone comprised of polyurethane foam in FIG. 6*b*.

The experimental and theoretical results, using a mesh-free analytical model for trabecular bone, in comparison with using the FEA meshed-based methods of the prior art, showed simulations using DEM correctly predicted the location and magnitude of compacted bone, simulating the experimental conditions with a degree of accuracy.

These experimental results provide support for the present invention, whereby trabecular bone is represented by a mesh-free model for analysis of implant migration through bone.

4. Example

In order to validate the present invention, an experimental model was developed whereby migration of an implant was physically simulated, whereby an indenter was urged through cadaveric human bone tissue by way of a mechanical penetration test.

Mechanical results and morphology results were compared with a computer simulation of the experimental model by way of a mesh-free analytical analysis in accordance with the present invention, whereby modelling and analysis was conducted using a mesh-free analytical method, in this case using Smoothed Particle Hydrodynamics (SPH) computer modelling techniques.

The following example exemplifies the experimental model and correlation thereof using the computer simulated process.

4.1 Experimental Overview

For the experimental model, compressive material penetration experiments were conducted using 5.0 mm diameter indenters having either sharp (conical in the present experiment) or flat profiled tip designs into human trabecular bone derived from the femoral head of cadaveric femurs.

A comparative theoretical model was utilized for comparison with the experimental model, using Smoothed Particle Hydrodynamics (SPH) computer modelling techniques.

A sample size of 6 was used for both the flat tip and sharp tip model, both experimentally and theoretically, a shown Table 1 below, Group 1 was utilized to establish reference force displacement scenarios for validation of simulation of the experiment which comprised Group 2.

Force-displacement data (F vs. D) was recorded continuously during the penetration tests by destructive compression of the bone material by the indenter to a depth of 10 mm for level of agreement and correlational analysis.

TABLE 1

Grouping of all penetration tests

| Group Number (Size) | Group |
|---|---|
| Group 1 (n = 6) | Human trabecular bone experiment-flat and sharp tip |
| Group 2 (n = 6) | Human trabecular bone simulation-flat and sharp tip |

4.2 Preparation of Human Trabecular Bone Specimens

Six fresh-frozen human cadaveric specimens were extracted from proximal femurs of female donors having a mean age of 82 years, with and age range of 75 to 90 years.

Diagnostic x-rays, using Ultrafocus 100 equipment, by Airton Bioptics, LLC, Arizona, US, were taken in the anteroposterior plane so as to allow for exclusion for lesions or any foreign bodies.

Figure 7A:
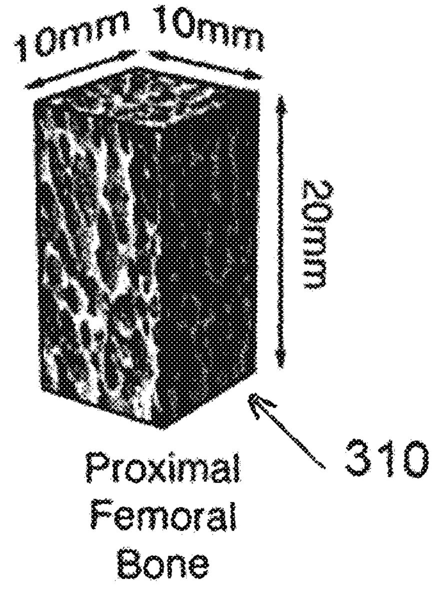
FIG. 7*a* depicts a schematic representation of trabecular bone used in experimental tests and for generation of a bone sample for numerical analysis, for evaluation of the theoretic model according to the present invention.

Referring to FIG. 7*a*, in order to prepare an experimental sample, a surgical saw was used to remove a central block of trabecular bone 310 from the femoral head of the proximal femurs, the central block measuring 10×10×20 mm, cut parallel to the axis of the femoral neck of the femurs.

Each specimen 310 had its orientation marked and recorded, and was encased with a 2.5 mm thick layer 320 of epoxy resin putty such that the 10×10 mm surface of the block corresponding to the distal end was left exposed for indentation testing.

Each specimen was then scanned using microCT at a 17.33 μm resolution to provide a record of its structure in an undamaged state and prior to indentation being conducted and such destructive mechanical testing. MicroCT calibration was completed as per the manufacturer's protocol, using a phantom of hydroxyapatite. Subsequently, morphometric analysis of each specimen was performed using CT Analyzer v1.14.1.4 (Bruker Corporation, Massachusetts, USA). Of the group of six experimental specimens of trabecular bone, half of all specimens were randomly assigned for testing using the flat-tipped indenters, and the remaining specimens were assigned for testing sharp-tipped indenters.

4.3 Mechanical Penetration Experimentation Setup

Figure 7B:
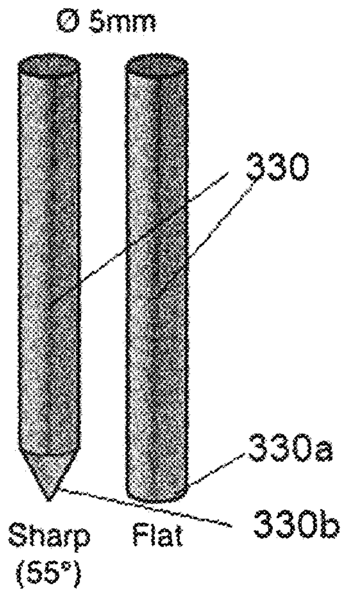
FIG. 7*b* shows a schematic representation of indenters as used in the experimental tests and theoretical analysis, for indenting and penetration within the bone sample of FIG. 7*a;*

Indenters 330 as used in the experimental tests, as represented by the illustrations in FIG. 7*b*, were fabricated from 5.0 mm diameter rods of 6061-T6 aluminum, selected for its radiolucent properties.

The material properties of aluminum the scientific literature indicated that the yield strength of 250 MPa and an elastic modulus of 70 GPa, which was considered to provide satisfactory rigidity given the stresses anticipated during the experimental model.

Rods were cut into 40 mm segments, and one end of each segment was turned on a lathe to provide either a flat tip 330*a* or a conical tip 330*b* with a 55 degrees vertex angle.

The geometries used for the tips 330*a*, 330 where utilized to simulate and replicate abstract typical blunt and self-tapping cancellous screws, respectively.

Figure 7C:
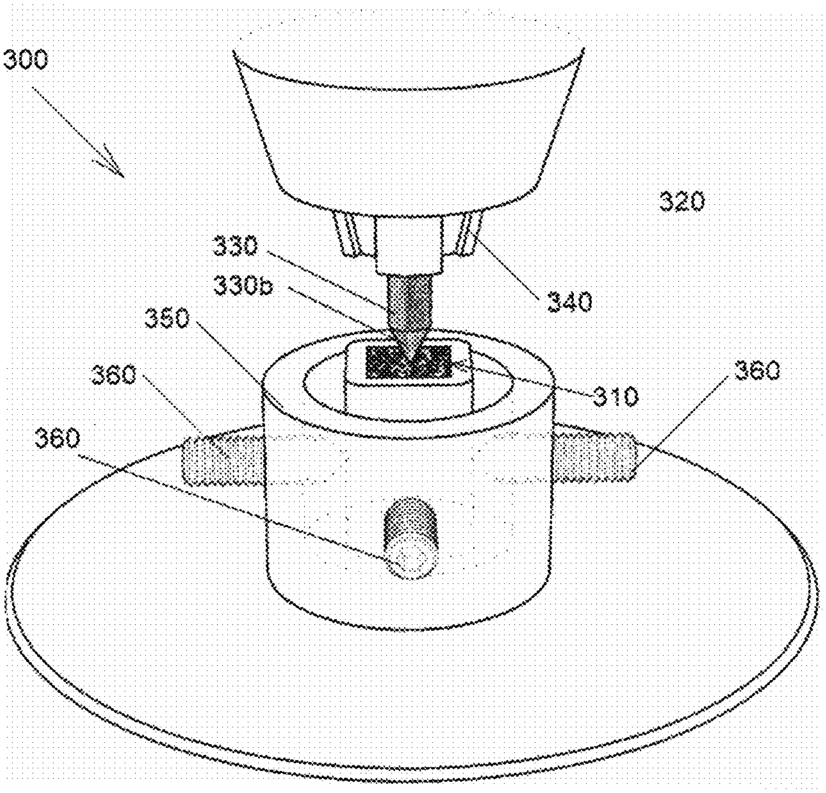
FIG. 7*c* shows a schematic representation of the experimental system for penetrating the bone sample of FIG. 7*a* with the indenters of FIG. 7*b;*
Figure 9A:
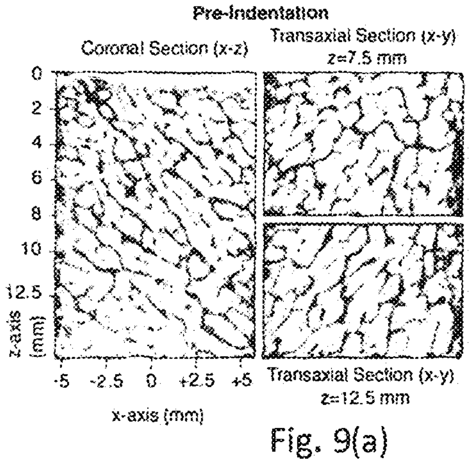
FIGS. 9(*a*)-9(*c*), there is shown analysis of microCT images of human trabecular bone specimens in the experimental model using a tapered tip indenter.
Figure 9D:
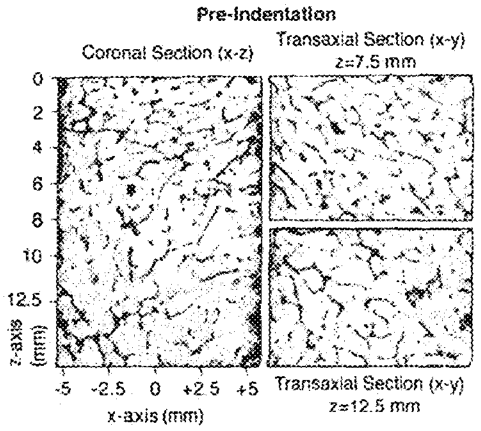
Figure 9B:
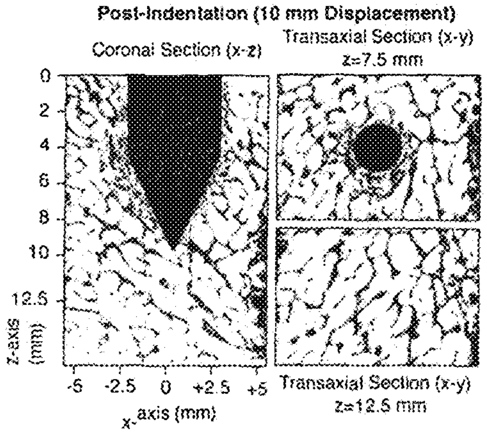
Figure 9E:
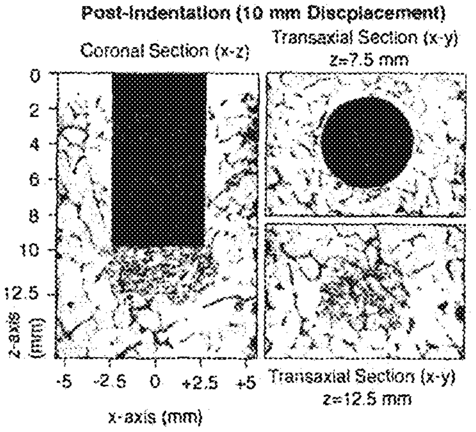
Figure 9C:
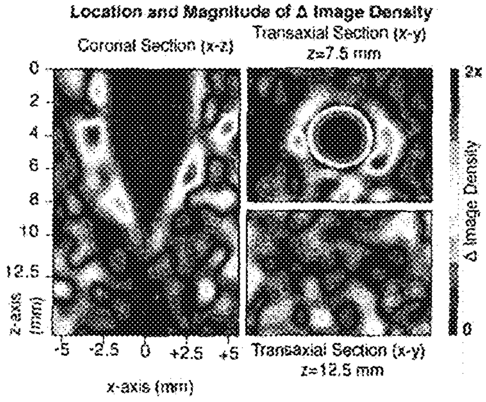
Figure 9F:
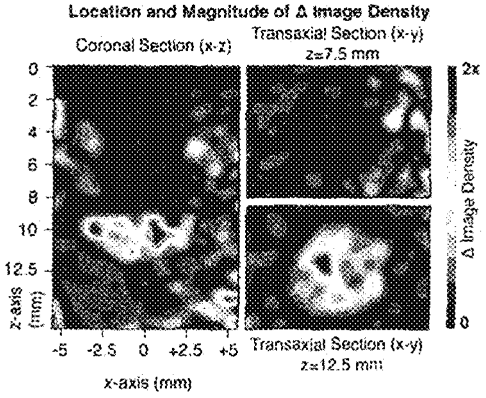
Figure 10A:
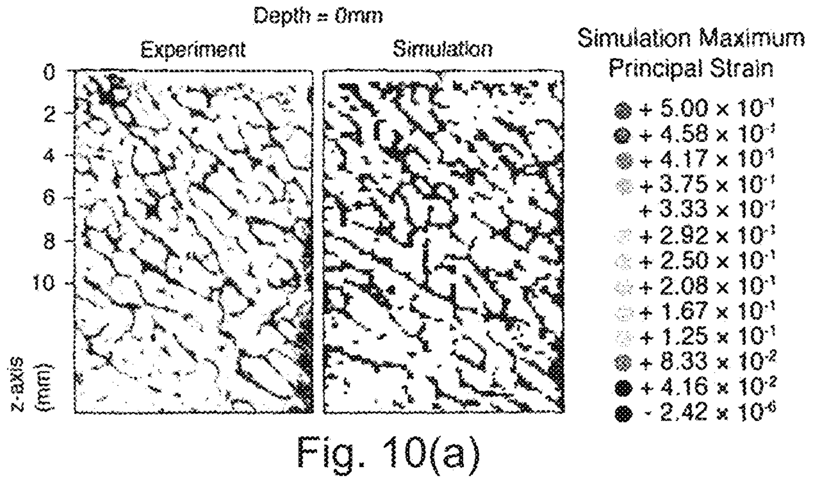
FIGS. 10(*a*) to 10(*e*), there is shown a comparison between experimental results and simulated results using human trabecular bone tissue for tests conducted with the tapered tip indenter using microCT images.
Figure 10B:
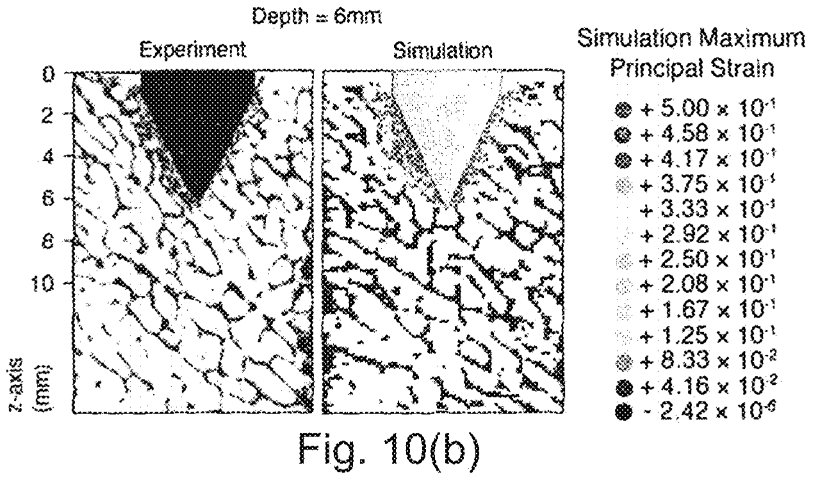
Figure 10C:
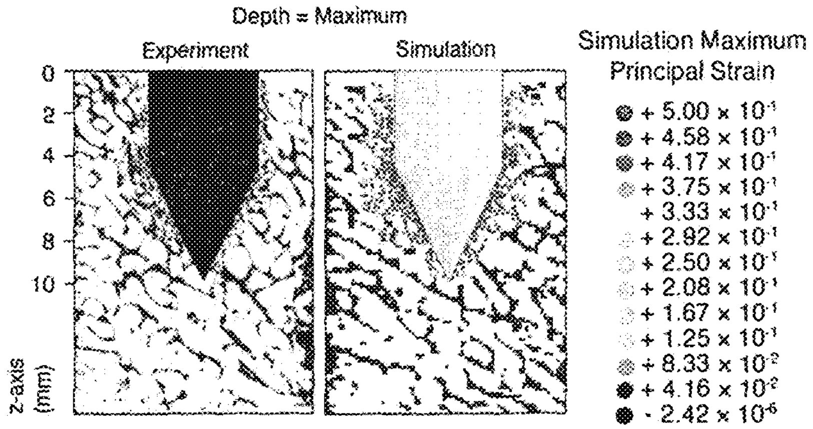
Figure 10D:
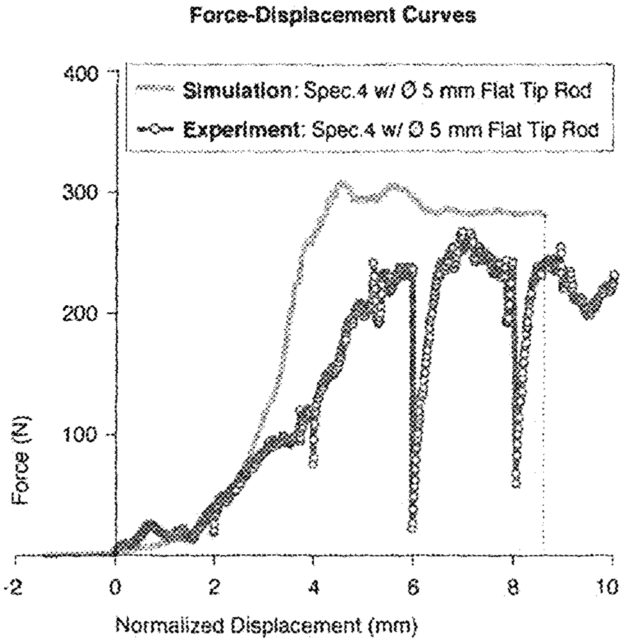
Figure 10E:
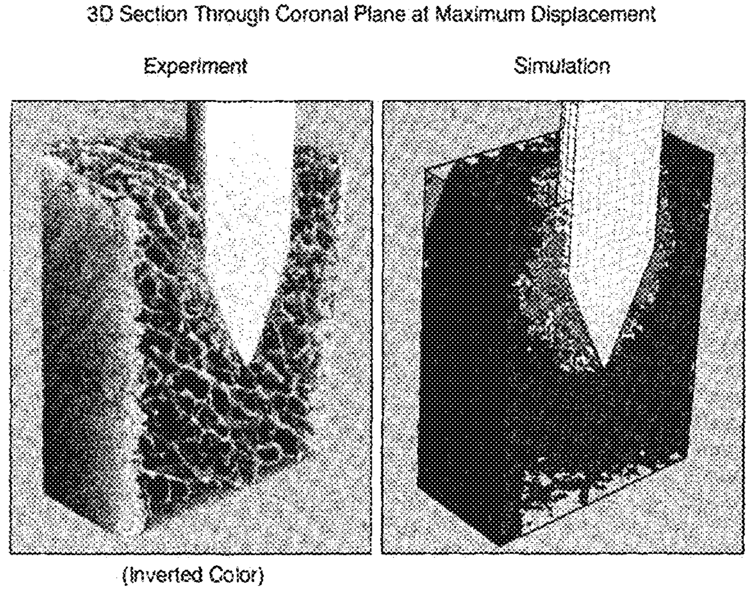
Figure 11A:
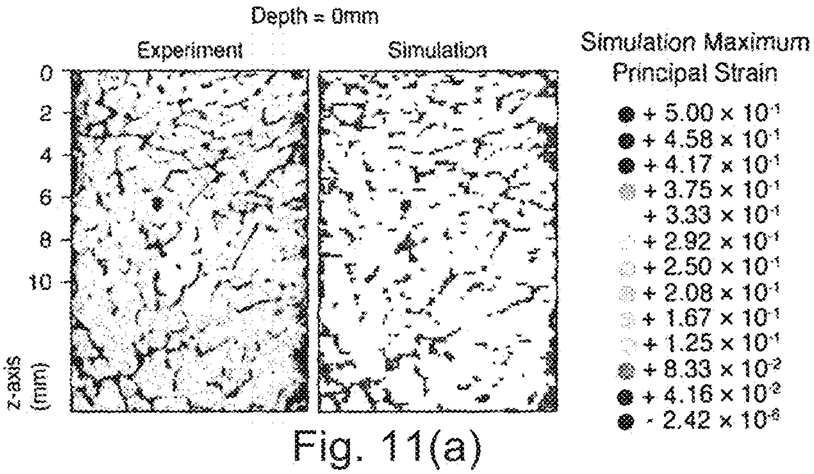
FIGS. 11(*a*) to 11(*e*), there is shown a comparison between experimental results and simulated results using human trabecular bone tissue for tests conducted with the flat-tipped indenter using microCT images.
Figure 11B:
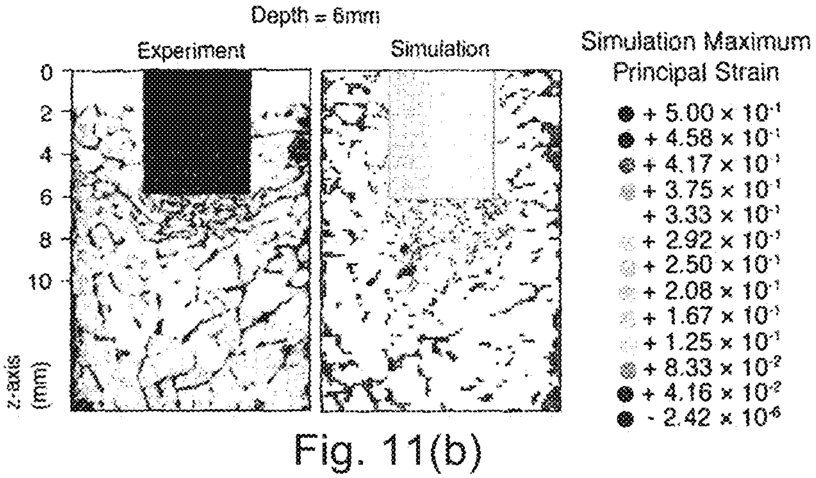
Figure 11C:
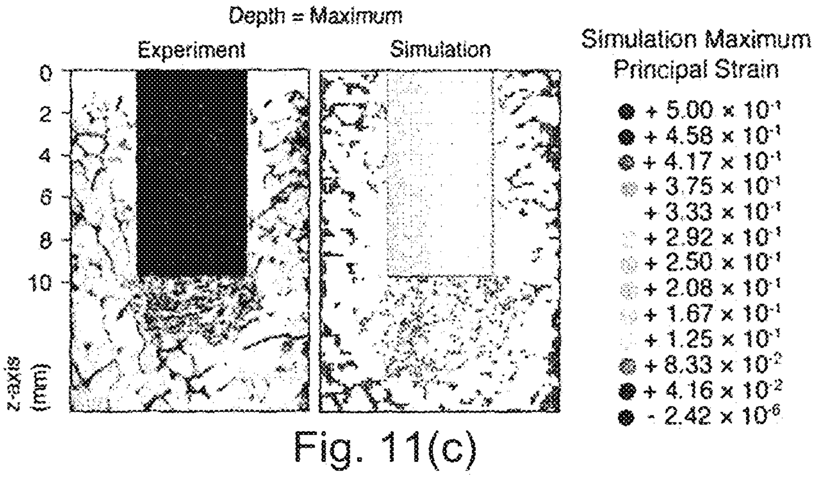
Figure 11D:
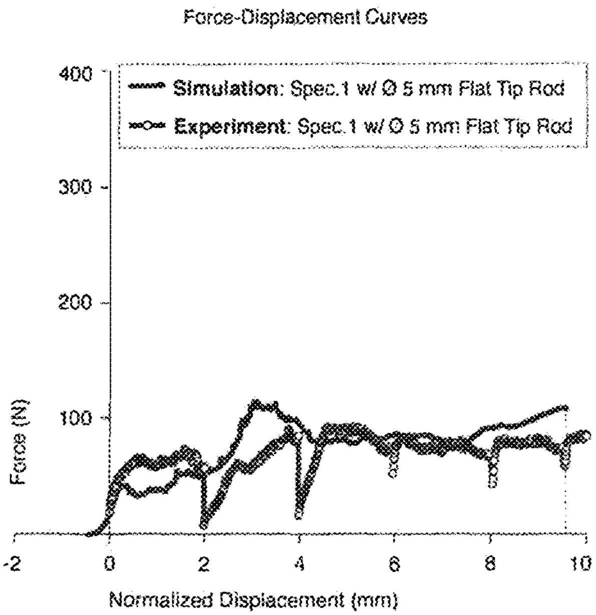
Figure 11E:
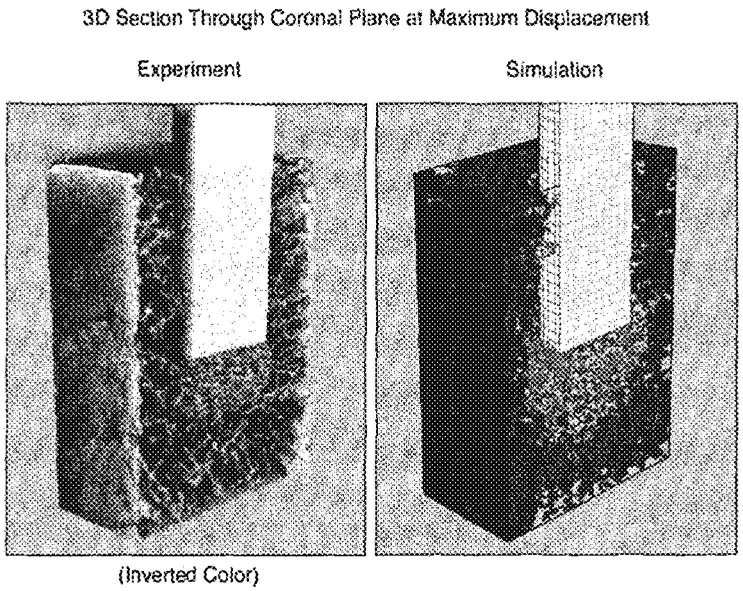
Figure 12A:
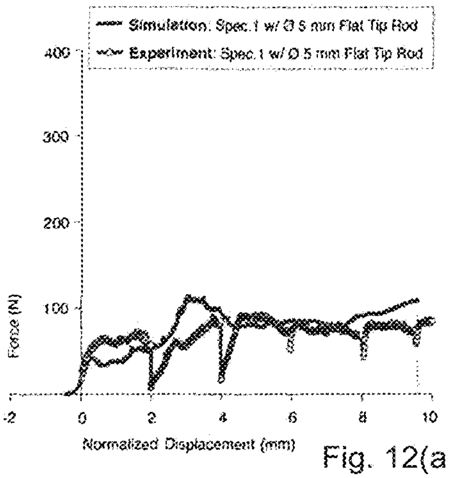
FIGS. 12(*a*) to 12(*c*), there is shown a comparison between Force versus Displacement simulation data and experimental data for the flat-tipped indenter for three human trabecular bone models.
Figure 12D:
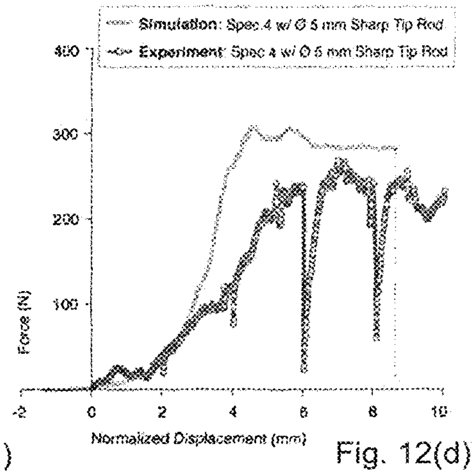
Figure 12B:
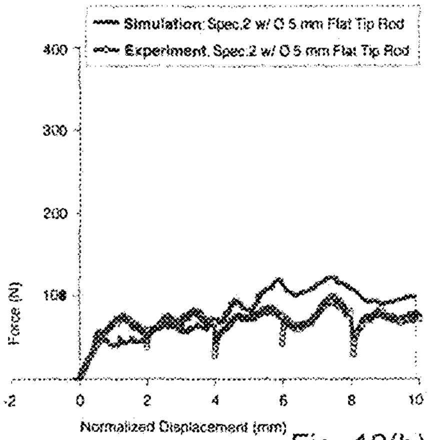
Figure 12E:
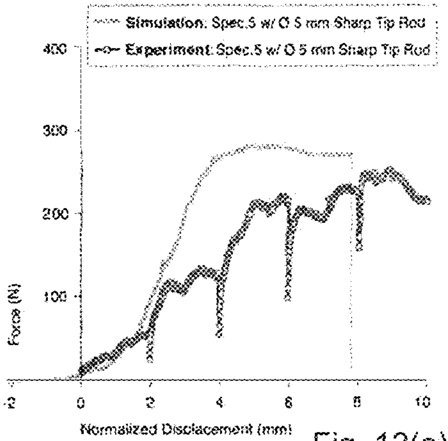
Figure 12C:
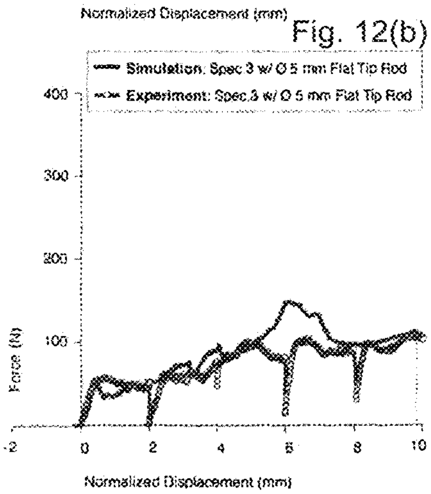
Figure 12F:
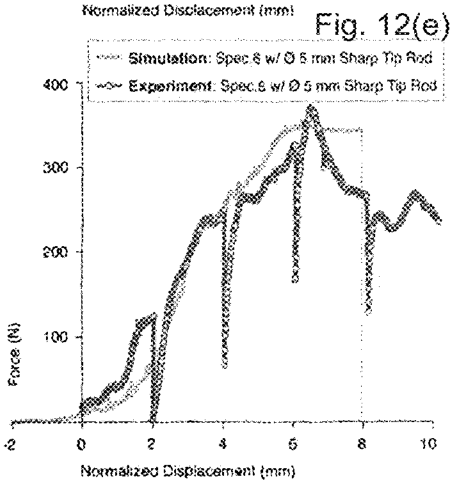

Referring to FIG. 7*c*, there is shown a schematic representation of the experimental system 300 as utilized. The 330 indenters were mounted with tips 330*b* facing vertically downward in a MTS 858 Mini Bionix by MTS, Inc., Minnesota, USA) hydraulic universal testing machine. A 2.5 kN load cell via a Jacobs chuck vise 340 was utilized, with the rear face of each indenter 330 supported thereby during loading.

Each specimen 310 was placed in a steel mounting frame 350 supporting its bottom face, and M6 set screws 360 supported the sides of the specimen 310 with minimal force, with the set screws 360 allowing for centering of the specimen 310.

The indenter was advanced into the specimen at a slow constant rate of 0.5 mm/min, which equated to a strain rate of 0.04%/second, in keeping with similar experiments in the literature such as use in Kelly N, Harrison N M, McDonnell P, McGarry J P. 2012. An experimental and computational investigation of the post-yield behaviour of trabecular bone during vertebral device subsidence. Biomechanics And Modeling In Mechanobiology 12 (4): 685-703, in order to minimize viscoelastic disturbances.

Throughout the experiments, displacement reached 10 mm, and force-displacement data was recorded with the force (F) as a function of indenter displacement (D). Based on a modified protocol from a similar study by Mueller T L, Basler S E, Müller R, van Lenthe G H. 2013. Time-lapsed imaging of implant fixation failure in human femoral heads. Med Eng Phys 35 (5): 636-643 a microCT system by Bruker Skyscan 1076, Bruker Corporation, Massachusetts, USA, was used to record structural damage to the specimen 310 during experimental penetration at 2 millimeter intervals, that is at 2 mm, 4 mm, 6 mm, 8 mm and 8 mm displacement intervals.

At each interval, specimens 310 were held stationary for 10 minutes to allow for stress relaxation of the specimens 310, and then removed from the mounting frame and following which were scanned at a 17.33 μm resolution. The indenters 330 were scanned along with the specimens 310, and care taken so as not to disturb the position or orientation of the indenter 330 relative to the bone specimens 310.

Following microCT scanning, each specimen 310 was returned to the mounting frame 350 and the hydraulic ram advanced downward at a very low displacement rate of 0.01 mm/s until precisely reaching the previous displacement prior to removal of the specimen 31 for scanning, and mechanical testing resumed. Following indentation and scanning, indenters 330 were removed, cleaned, and inspected for signs of failure or wear.

4.4 Simulated SPH Penetration Model Setup

Penetration experiments of human trabecular bone were simulated using the mesh-free smoothed particle hydrodynamics (SPH) model using the numerical analysis software ABAQUS 6.13, by Dassault Systèmes, France.

For the present exemplary model, SPH was selected and utilized as the basis of the theoretical model due to the present inventors considering it applicable for high-strain, crushing and fragmentation damage behaviors of bone during compaction and penetration, in keeping with the observed short-comings of mesh-based models of the prior art as discussed above In order to form the model for use in the SPH analysis, MicroCT scans of the six 10×10×20 mm human trabecular bone specimens 310 in their intact states and prior to mechanical testing were imported as uncompressed greyscale image stacks to construct 3D models.

Minor rotational misalignments of the image stacks were corrected using DataViewer v1.5.2.4 by Bruker Corporation, Massachusetts, USA, and new volumes of interest (VOI) measuring 664×664×1264 px were exported.

VOIs were selected such that they included an approximately 1 mm thick layer of resin material on all sides in order to produce boundary conditions similar to those of the above experimental model.

VOIs were then imported into CT Analyzer, and a thresholding function with a range of 75-255 was applied, corresponding to the approximate density of the trabeculae as confirmed by the hydroxyapatite phantom as provided by the manufacturer.

A material model with the properties below was applied to the SPH network in a manner consistent with the literature such as in Ruffoni D, Müller R, van Lenthe G H. 2012. Mechanisms of reduced implant stability in osteoporotic bone. Biomech Model Mechanobiol 11 (3-4): 313-323. A softened elastoplastic model was adopted to reproduce the material nonlinearity of trabecular bone. The stress-strain law is defined as follows:

$$\sigma = E:(\varepsilon - \varepsilon^p) \tag{1}$$

where $\sigma$ is stress tensor; $\varepsilon$ and $\varepsilon^p$ are strain and plastic strain, respectively; E is elasticity tensor. The associate evolution of plastic strain can be expressed as follows $$\begin{cases} \dot{\varepsilon}^p = \dot{\lambda}\dfrac{\partial f^p(\sigma)}{\partial \sigma} \\ f^p(\sigma) - r(\kappa) = \sqrt{J_2} - r(\kappa) \le \\ \kappa = \sqrt{\dfrac{2}{3}\varepsilon^p : \varepsilon^p} \end{cases} \tag{2}$$

where $J_2$ is the second invariance of deviatoric stress s.

It is observed that the von Mises type yield function is defined in Eq. (2). The hardening/softening function r (·) may be resolved by the uniaxial stress strain relation.

Computer Aided Design (CAD) models of the indenters 330 were imported into ABAQUS as rigid body structures. These simulated indenters were moved into the derived SPH bone network to a displacement depth of 10 mm while recording the required force to achieve such a displacement depth.

During the simulated loading using ABAQUS, the specimen 310 was fully constrained on its bottom surface, and the indenter 330 was limited to movement inly along its main axis, the z-direction, which corresponds to the direction of indentation. The coefficient of friction as utilized between indenter and simulated bone was 0.15.

A semi-blinded methodology was employed for simulation calibration. Two random specimens, in this case Specimen No. 1 and Specimen No. 4, with different indenter tips were selected and used in repeated runs of the simulation to derive a set of material parameters capable of generating predicted load (F) values until an average error of less than 20% was achieved.

The resultant derived material parameter values as shown below in Table 2 were then uniformly applied to the simulation model for the remaining 4 specimens, with no further calibration.

Initial validation of the SPH model was conducted by correlating the six final simulated force-displacement curves with the results from the experimental model.

TABLE 2

Material parameters of ABAQUS model for simulated human trabecular bone.

| Material Model Parameter | | Values |
|---|---|---|
| Young's Modulus | E | 300 MPa |
| Poisson's Ratio | v | 0.3 |
| Yielding stress | $f_y$ | 5 MPa |
| Fracture strain | $\varepsilon_f$ | 0.5 |
| Residual stress | $f_r$ | 1 MPa |

4.5 Statistical Analysis of Results from Example

Force-displacement (F-D) data obtained from both mechanical experimental model (Group1) and from the simulation model (Group2) were matched by Displacement (D) values.

All D values were zeroed at a starting Load (F) value of 5N to eliminate the initial 'slack' or "toe-in" effect in models. The relaxation of bone material during microCT scans was shown in similar axial loading studies such as by Ryan M K, Mohtar A A, Cleek T M, Reynolds K J. 2016. Time-elapsed screw insertion with microCT imaging. Journal of Biomechanics 49 (2): 295-301 and Mueller T L, Basler S E, Müller R, van Lenthe G H. 2013. Time-lapsed imaging of implant fixation failure in human femoral heads. Med Eng Phys 35 (5): 636-643, to produce local dips or decreases in load values, but to not affect the overall shape or maximum values of the F-D curve. Local dips in load values at 2 mm increments due to microCT scanning were therefore omitted from calculations of agreement between experimental and simulated results.

SPSS software v24 by IBM, Armonk, NY, USA, and MedCalc software v17.6 by Ostend, Belgium, were used for statistical calculation and analysis. Minimum and maximum ranges (spread) in micro-CT morphometry values, and load (F) for each group were expressed in descriptive terms. Spearman's rho two-tailed correlation coefficient was determined for pooled F values against bone density for each mm of penetration.

Agreement between the experimental and simulated F was determined by two methods. Firstly, a scatter plot between experimental F and simulated F values was constructed, and the concordance correlation coefficient determined as a product of the Pearson correlation coefficient and the bias factor as defined by Steichen T J, Cox N J. 2002. A note on the concordance correlation coefficient. Stata J 2.2 (2002): 183-189.

Secondly, a Bland-Altman plot, Bland J M, Altman D G. 1999. Measuring agreement in method comparison studies. Statistical Methods in Medical Research 8.2 (1999): 135-160, was constructed to determine the mean and the upper and lower bound 95% limits of agreement (LoA) between the two methods.

4.6 Image Analysis of Experimental Results

Contour maps of the change in density in the human bone specimens following indenter penetration were generated using the Matlab R2016b Bioinformatics Toolbox. Prior to import of the data into Matlab, pixels occupied by the indenters were deleted, and image stacks were blurred (Gaussian, 20 px) to facilitate contour map generation using Photoshop CC2015.5, by Adobe, Inc, California, USA.

MicroCT images used for figure display underwent filtering in DataViewer to facilitate viewing of mineralized bone compaction patterns; all images were inverted and their 8-bit greyscale ranges were adjusted to 51-150.

4.7 Experimental Results

Referring to FIG. 8, there is shown tabulated detailed MicroCT morphometry data in respect of Bone Volume (BV), Bone Volume/Total Volume (BV/TV), Trabecular Thickness (Tb.Th), Trabecular Spacing (Tb.Sp), Trabecular Number (Tb.N), Load (Force) measured per each 1 mm displacement and Correlation between BV/TV and Force for the pooled data.

The MicroCT densitometry revealed a bone volume to total volume (BV/TV) ratio of specimens ranging from 17.88% to 30.49%. For the six experimental and simulation pairs (a total of 12), we a total sample size of 5345 data points was obtained.

Load values (F) showed high variation between the six simulated scenarios. Between samples, peak F measured by the experimental method varied between 92.0N to 365.0 N, while peak F measured by SPH simulation varied from 115.5N to 352.2N. The F value measured at each 1 mm of displacement for each specimen is shown in FIG. 8.

The pooled F values correlated significantly with CT morphometric bone density (BV/TV) from 3 to 8 mm ($p<0.001$) with a correlation coefficient of 0.792 to 0.919 (strong correlation).

Due to zeroing of the D=0 values at F=5N to account for toe-in, simulated F results were shifted forward and unavailable for analysis beyond 8 mm.

Referring to FIGS. 9(*a*)-9(*c*), there is shown analysis of microCT images of human trabecular bone specimens in the experimental model using a tapered tip indenter. FIG. 9(*a*) shows an image of the bone sample prior to application of the indenter, and FIGS. 9(*b*) and 9(*c*) show images after advancement of the indenter into the bone tissue.

The results showed consistent trends in the magnitude and location of bone compaction; penetration of the bone specimens by sharp indenters which resulted in density increases along the sides of the indenter penetration path, while the bone tissue directly beneath the indenter tip was generally unchanged.

Referring to FIGS. 9(*d*)-9(*f*), there is shown analysis of microCT images of human trabecular bone specimens in the experimental model using a flat tipped indenter. FIG. 9(*d*) shows an image of the bone sample prior to application of the indenter, and FIGS. 9(*e*) and 9(*f*) show images after advancement of the indenter into the bone tissue.

Conversely to the results with respect to the tapered tip indenter, penetration of bone specimens by flat indenters demonstrated increases in density directly beneath the indenter, with little to no change along the sides of the indenter penetration path. Referring to FIGS. 10(*a*) to 10(*e*), there is shown a comparison between experimental results and simulated results using human trabecular bone tissue for tests conducted with the tapered tip indenter using microCT images, whereby FIG. 10(*a*) shows comparison between the experimental and simulated model at a 0 mm depth penetration, FIG. 10(*b*) shows comparison between the experimental and simulated model at a 6 mm depth penetration, FIG. 10(*c*) shows comparison between the experimental and simulated model at maximum depth penetration, FIG. 10(*d*) shows an example of comparison of the experiment and simulation models of Load versus displacement, and FIG. 10(*e*) shows a perspective view comparison between the experimental model and the simulation model at maximum penetration through the coronal plane.

Referring to FIGS. 11(*a*) to 11(*e*), there is shown a comparison between experimental results and simulated results using human trabecular bone tissue for tests conducted with the flat tipped indenter using microCT images, whereby FIG. 11(*a*) shows comparison between the experimental and simulated model at a 0 mm depth penetration, FIG. 11(*b*) shows comparison between the experimental and simulated model at a 6 mm depth penetration, FIG. 11(*c*) shows comparison between the experimental and simulated model at maximum depth penetration, FIG. 11(*d*) shows an example of comparison of the experiment and simulation models of Load versus displacement, and FIG. 11(*e*) shows a perspective view comparison between the experimental model and the simulation model at maximum penetration through the coronal plane.

The coronal slices of the simulated trabecular bone during indenter insertion revealed trends in the magnitude and location of bone compaction that were qualitatively similar to those of the experimental scenarios; whereby penetration of the bone specimens by sharp indenters as shown in FIGS. 10(*a*) to 10(*e*) resulted in bone density increases along the sides of the indenter penetration path, while the bone tissue directly beneath the indenter tip was generally unchanged.

Conversely, penetration of bone specimens by flat indenters as shown in FIGS. 11(*a*) to 11(*e*) resulted in increases in bone density directly beneath the indenter, with little to no change along the sides of the indenter penetration path.

Referring to FIGS. 12(*a*) to 12(*c*), there is shown a comparison between Force versus Displacement simulation data and experimental data for the flat-tipped indenter for three human trabecular bone models, and for FIGS. 12(*d*) to 12(*f*), there is shown a comparison between Force versus Displacement simulation data and experimental data for the conical-tipped indenter for three human trabecular bone models.

Figure 13A:
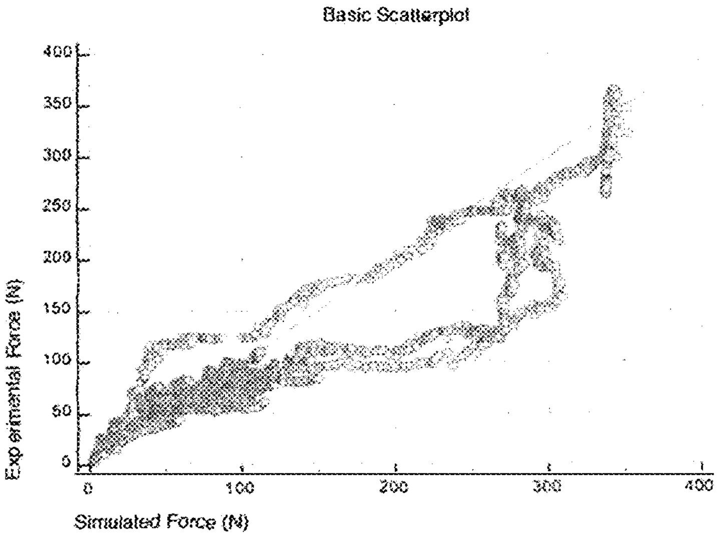
FIG. 13(*a*) shows a basic scatter plot graph for correlation between experimental data.
Figure 13B:
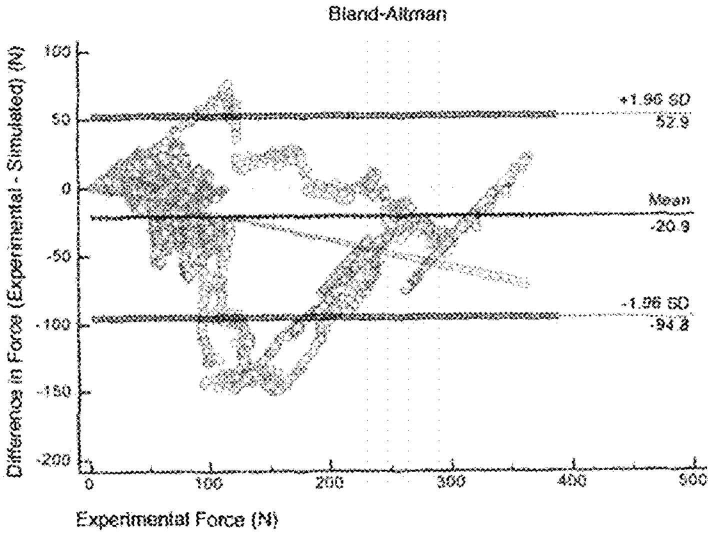

Referring to FIG. 13(*a*) there is shown a basic scatter plot graph for correlation between experimental data and in FIG. 13(*b*) there is shown a Bland-Altman plot for correlation between experimental data.

Using all data from D=0 onwards, that is displacement from zero onwards, between the experimental and simulated groups, the concordance correlation coefficient is 0.888 (95% CI 0.883 to 0.893), Pearson p (precision) is 0.9396 (95% CI 0.9364 to 0.9427) and Bias correction factor Cb (accuracy) is 0.945, and significance level $P<0.0001$.

The Bland-Altman LoA is-20.94N with 95% (1.96 SD) lower and upper bound value between-94.81N to 52.93N and the coefficient of repeatability was 84.5 with the simulated results biased towards an overestimation of F at higher values.

5. Summary of Findings and Discussion

The novel computational model of the present invention utilizing a mesh-free model representative of trabecular bone for predicting implant penetration in bone to accurately predict, and assist in mechanically characterizing, the performance of various implant tip designs in human trabecular bone of a range of quality has been validated by the experimental findings.

The validating experimental model has utilized tip designs that were both geometrically distinct and simple; distinctiveness being likely to produce a range of results conducive to rigorous testing of the simulation's accuracy, and simplicity being likely to facilitate interpretation of the data, given the present limitations in the understanding of the mechanisms of fracture and compaction in trabecular bone, and absence of suitable modelling techniques in the prior art for bone-implant systems in respect of trabecular bone In the Assessment of Applicability of Mesh-Free Model at item 1 above, whereby flat tip designs and conical tips with a 55 degree vertex angle fit an applicable modelling, it was demonstrated that mesh-based bone-implant modelling systems were inadequate in relation to modelling of the behavioral aspects of such bone tissue as identified by the present inventors.

The cadaveric bone experiment established the applicability of a mesh-free model for prediction of trabecular bone behavior and implant migration in bone.

Further, the cadaveric bone experiment established the following expectations for the results of the simulation:

(1) tip design mainly affects the overall shape of the force-displacement curve, with flat tips producing curves with initially steeper slopes that quickly flatten out, and sharp tips producing curves with slopes that gradually increase with displacement depth; while (2) the density of the testing substrate mainly affects the magnitude of the displacement curve.

Distinct differences in compaction patterns were observed between tip designs, with flat tips generating a growing region of compacted material, referred to here as a bolus, directly below the tip, and sharp tips instead compacting material only along the sides of the indenter.

Concentration of compacted material along the side of the indenter was in keeping with the findings of similar push-in studies in polyurethane foam in the scientific literature by Kelly N, Cawley D T, Shannon F J, McGarry J P. 2013. An investigation of the inelastic behaviour of trabecular bone during the press-fit implantation of a tibial component in total knee arthroplasty. Med Eng Phys 35 (11): 1599-1606.

The simulated indentation experiment using a mesh-free model for trabecular bone demonstrated that mesh-free modeling methods can be used to accurately predict key mechanical characteristics of at least implant of the general form of the utilized indenters in trabecular bone under axial loading, when compared with experimental results.

Force-displacement curve agreement was confirmed statistically, and patterns of bone compaction were qualitatively similar. The simulated results provided several insights into the characterization of implant tip performance in trabecular bone:

(1) For flat indenters, relatively high levels of stress were observed among SPH particles in direct contact with the surface of the tip during initial loading, leading to high strain values as material in this region was crushed to form a dense bolus.

Stress concentrations then shifted to two regions, the undamaged material directly below the bolus as well as a ring of material along its edge as this material was sheared away from the rest of the trabecular network.

This suggests that the failure of flat-tipped implants under axial loading in trabecular bone may be described as the partial compaction and shearing-off of material directly below the tip surface, and the gradual accretion of this material into a dense cylindrical bolus of increasing length.

The production of compacted bone extending beyond the end of the implant, as observed in the flat-tipped indenters, may be deleterious to implant performance. The results support the assertion that in the case of cut-out due to loading along the axis of an implant, such a compacted bolus would begin to transmit stress to the subchondral and cortical layers of bone well in advance of the implant itself.

(2) Sharp-tipped indenters in both the real bone experiment and simulation, conversely, generated compacted material along their peripheries. Additionally, stress concentration was observed at the apexes of sharp-tips, where SPH particles were observed undergoing significant tensile stresses.

This phenomena supports that the failure of sharp-tipped implants under axial loading in trabecular bone may be characterized by a wedge-like mechanism whereby material is split apart from the center and partially crushed as it is pushed to the sides of the penetration path, where it is deposited in a compacted state.

Confirmation of the ability of the mesh-free simulation trabecular bone model used accurately predict scenarios, and the invention is not limited to particular geometries or axial loading, but in other and alternate embodiments it is also applicable to implants having complex geometries with complex loading regimes.

Accordingly, the present invention provides a system that is useful in increasing the predictability of clinicians' and biomechanical engineers' predictions of the amount of migration of such an implant relative to its original position within bone tissue, as well as the likelihood of risk of "cut-out" or unwanted penetration of the implant and complications thereof when physiological or traumatic loads are applied, localized excessive loading, as well as stress shielding and/or aseptic loosening, and the system can provide for:

(i) Assessment of suitability of fixation implants for a particular clinical fixation requirement;

(ii) Selection of appropriate fixation implants for a particular clinical fixation requirement;

(iii) Assessment of suitability of prosthetic implants for a particular clinical fixation requirement;

(iv) Selection of suitable prosthetic implants for a particular clinical requirement;

(v) Design of fixation implants (vi) Design of prosthetic implants

Accordingly, the present invention provides a method and system for orthopaedic surgical planning and implant design, and in particular to method and system for orthopaedic surgical planning and implant design based on anatomic data, which overcomes deficiencies of the mesh-based methods and systems of the prior art.

The invention claimed is:

1. A computer-implemented bone-implant system evaluation method for application of mesh-free analysis of trabecular bone of a bone-implant system, said method being for determining a biomechanical result, and said method comprising:

(i) using a bone-implant model to determine a biomechanical result, wherein bone-implant model includes
a mesh-free trabecular bone model which comprises a plurality of bone data nodes which represents trabecular bone and comprises material properties of trabecular bone wherein bone data nodes of plurality of bone data nodes are free to interact with any neighboring bone data nodes of said plurality of bone data nodes upon contact with said neighboring bone data nodes and wherein said bone data nodes are broken off, moved, and redistributed from neighboring bone data nodes within the mesh-free trabecular bone model upon computer simulated loading of the bone-implant system, wherein the redistribution of bone data nodes is representative of fragmentation and redistribution of trabecular bone, for evaluation of performance of the bone-implant system for an implant implanted within the bone structure at an anatomical site; and
an implant data set which is indicative of the position of the implant with respect to said anatomical site, wherein implant data set comprises data representative of the geometry and materials properties of the implant; and (ii) determining a biomechanical result based upon said computer simulated loading of the bone-implant system based upon mesh-free analysis of the bone-implant model by utilization of a mesh-free analytical method, wherein the biomechanical result comprises data based on the displacement of the implant relative to the bone of bone-implant model.

2. The method according to claim 1, wherein the bone structure data is acquired from a surgical site of a subject and the bone-implant model is a subject specific bone-implant model.

3. The method of claim 1, wherein the bone structure data is acquired from a contralateral side of a surgical site of a subject and the bone-implant model is a subject specific bone-implant model.

4. The method of claim 1, wherein the bone structure data is acquired from a pre-existing data set and wherein said pre-existing data is non-subject specific and wherein the bone-implant model is non-subject specific, wherein the pre-existing data set is selected based upon a correlation of subject data and data of the pre-existing data set, and wherein the subject data includes data selected from the group including surgical site location, geometrical properties of the bone at the surgical site, mechanical properties of the bone at the surgical site, subject age, subject gender, subject activity level or combinations thereof.

5. The method according to claim 1, wherein the bone structure data is acquired by way of a bone imaging technique selected from the group include X-ray, Computer Tomography (CT) scan, Magnetic Resonance Imaging (MRI), Bone Mineral Density (BMD) scan including by way of Dual Energy E-Ray Absorption (DEXA).

6. The method according to claim 5, wherein the material properties of the trabecular bone for the mesh-free model of trabecular bone are determined from data acquired by said bone imaging technique or are acquired from a library of pre-existing data and based on statistical analysis.

7. The method according to claim 1, wherein the implant data set is selected from a plurality of implant data sets, and wherein each implant data set of said plurality of implant data sets includes data indicative of implant type and variances thereof including implant design, implant size, implant geometry and combinations thereof, and wherein the biomechanical result provides a surgical report indicative of the appropriateness of the implant defined by the implant data set for said biomechanical requirements for the anatomical site.

8. The method according to claim 1, wherein the method provides for assistance in implant design, wherein a first implant data set is input and the position of the first implant data set is input such that the implant is positioned at a first anatomical position, and wherein the biomechanical result includes mechanical data.

9. The method according to claim 1, wherein the biomechanical result includes mechanical data in relation to the bone, the implant or the bone and the implant, including at least one of stress, strain, deflection or displacement data.

10. The method according to claim 1, wherein the implant is a component of a bone fixation system, hip screws, dynamic hip screws, pedicle screw, screws, plates, rods, plate/screw assemblies, wires, bars, a prosthesis or component of a prosthesis system, total or partial hip replacements, knee implants include total knee replacement implants, partial knee replacements, shoulder implant prostheses including full and partial joint replacement prostheses, spinal fusion system and the like.

11. The method according to claim 1, wherein the mesh free analysis is selected from the group including mesh-free systems including Smoothed Particle Hydrodynamics (SPH), Element-Free Galerkin (EFG), Reproducing Kernel Particle Method (RKPM) and Discrete Element Method (DEM).

12. A system for computer-implemented bone-implant system evaluation for evaluation of performance of a bone-implant system for an implant implanted within the bone structure of a subject at an anatomical site using mesh-free analysis of trabecular bone of a bone-implant system and for determining a biomechanical result, the system comprising:

a processor; and a data output module in communication with the processor, wherein the system is configured to use a bone-implant model, wherein the bone-implant model includes a mesh-free trabecular bone model which comprises a plurality of bone data nodes which represents trabecular bone and comprises material properties of trabecular bone wherein bone data nodes of plurality of bone data nodes are free to interact with any neighboring bone data nodes of said plurality of bone data nodes upon contact with said neighboring bone data nodes and wherein said bone data nodes are broken off, moved, and redistributed from neighboring bone data nodes within the mesh-free trabecular bone model upon computer simulated loading of the bone-implant system, wherein the redistribution of bone data nodes is representative of fragmentation and redistribution of trabecular bone, wherein the system comprises a bone structure input interface; and an implant data set which is indicative of the position of the implant with respect to said anatomical site, wherein implant data set comprises data representative of the geometry and materials properties of the implant; and wherein the processor is configured to provide output data to the output module, wherein the output data comprises a biomechanical result based upon said simulated loading of the bone-implant system based upon mesh-free analysis by utilization of a mesh free analytical method, of the bone-implant model, wherein the biomechanical result includes data based on the displacement of the implant relative to the bone of bone-implant model.

13. The system according to claim 12, wherein the bone structure data is acquired from a pre-existing data set and wherein said pre-existing data is non-subject specific bone structure data and wherein the bone-implant model is non-subject specific, and wherein the system further includes a data store in communication with the processor and carries said a pre-existing data set.

14. The system according to claim 12, wherein the subject data includes data selected from the group including surgical site location, geometrical properties of the bone at the surgical site, mechanical properties of the bone at the surgical site or combinations thereof, subject age, subject gender, subject activity level or combinations thereof.

15. The method according to claim 12, wherein the bone structure data is data acquired by way of a bone imaging technique, and wherein the material properties of the trabecular bone for the mesh-free model of trabecular bone are determined from data acquired by said bone imaging technique.

16. The system according to claim 12, wherein the implant data set is selected from a plurality of implant data sets, and wherein each implant data set of said plurality of implant data sets includes data indicative of implant type and variances thereof including implant design, implant size, implant geometry and combinations thereof, and wherein the biomechanical result is a surgical report indicative of the appropriateness of the implant defined by the implant data set for said biomechanical requirements for the anatomical site.

17. The system according claim 12, wherein the processor selects an implant data set from a plurality of implant data sets and determines the mechanical properties of the bone, implant or bone and implant based on the displacement of the implant repetitively and automatically until a requisite implant data set is determined and a preferable implant positioning is obtained which provides said biomechanical requirements based on predefined design parameters, and wherein upon a requisite implant data set being determined, a biomechanical report is provided by the processor which include an implant recommendation report, wherein said implant recommendation report includes one or more of implant type, implant size, implant configuration, implant positioning, and combinations thereof.

18. The system according to claim 12, wherein the system provides for assistance in implant design, wherein a first implant data set is input and the position of the first implant data set is input such that the implant is positioned at a first anatomical position, and wherein the biomechanical result includes mechanical data.

19. The system according to claim 12, wherein the biomechanical result includes mechanical data in relation to the bone, the implant or the bone and the implant, including at least one of stress, strain, deflection or displacement data.

20. The system according to claim 12, wherein the implant is a component of a bone fixation system, hip screws, dynamic hip screws, pedicle screw, screws, plates, rods, plate/screw assemblies, wires, bars, a prosthesis, component of a prosthesis system, hip replacement prostheses for hip joints which may be total or partial hip replacements, knee implants include total knee replacement implants, partial knee replacements, shoulder implant prostheses including full and partial joint replacement prostheses, spinal fusion system and the like.

21. The system according to claim 12, wherein the mesh free analysis process is selected from the group including mesh-free systems including Smoothed Particle Hydrodynamics (SPH), Element-Free Galerkin (EFG), Reproducing Kernel Particle Method (RKPM) and Discrete Element Method (DEM).

22. A computerized system for implementing evaluation of a bone-implant system and for determining a biomechanical result, said computerized system including at least one of a processor module, and wherein the system is configured for performing the steps of:

(i) using mesh-free analysis of trabecular bone of the bone-implant system using a bone-implant model including a mesh-free trabecular bone model which comprises a plurality of bone data nodes which represents trabecular bone and comprises material properties of trabecular bone wherein bone data nodes of plurality of bone data nodes are free to interact with any neighboring bone data nodes of said plurality of bone data nodes upon contact with said neighboring bone data nodes and wherein said bone data nodes are broken off, moved, and redistributed from neighboring bone data nodes within the mesh-free trabecular bone model upon computer simulated loading of the bone-implant system, wherein the redistribution of bone data nodes is representative of fragmentation and redistribution of trabecular bone, for evaluation of performance of the bone-implant system for an implant implanted within the bone structure at an anatomical site; and an implant data set which is indicative of the position of the implant with respect to said anatomical site, wherein implant data set comprises data representative of the geometry and materials properties of the implant (ii) determining by the processor module a biomechanical result based upon said computer simulated loading of the bone-implant system based upon mesh-free analysis of the bone-implant model by utilization of a mesh free analytical method, wherein the biomechanical result comprises data based on the displacement of the implant relative to the bone of bone-implant model.

* * * * *